(12) United States Patent
Inomata et al.

(10) Patent No.: US 7,884,201 B2
(45) Date of Patent: Feb. 8, 2011

(54) METHOD FOR SEPARATING AND PURIFYING RNA

(75) Inventors: Hiroko Inomata, Asaka (JP); Tomoko Mori, Asaka (JP)

(73) Assignee: Fujifilm Corporation, Tokyo (JP)

( * ) Notice: Subject to any disclaimer, the term of this patent is extended or adjusted under 35 U.S.C. 154(b) by 273 days.

(21) Appl. No.: 11/995,310

(22) PCT Filed: Aug. 30, 2006

(86) PCT No.: PCT/JP2006/317584

§ 371 (c)(1),
(2), (4) Date: Jan. 10, 2008

(87) PCT Pub. No.: WO2007/026929

PCT Pub. Date: Mar. 8, 2007

(65) Prior Publication Data

US 2009/0143572 A1   Jun. 4, 2009

(30) Foreign Application Priority Data

Aug. 30, 2005   (JP) ............... 2005-249694
Aug. 25, 2006   (JP) ............... 2006-229142

(51) Int. Cl.
*C07H 21/00* (2006.01)
(52) U.S. Cl. ............... 536/25.4; 536/25.41; 536/25.42
(58) Field of Classification Search ............ None
See application file for complete search history.

(56) References Cited

U.S. PATENT DOCUMENTS

| 6,218,531 | B1 | 4/2001 | Ekenberg |
| 2002/0192667 | A1 | 12/2002 | Kojima et al. |
| 2003/0170669 | A1 | 9/2003 | Garvin |
| 2005/0037351 | A1 | 2/2005 | Kanno et al. |

FOREIGN PATENT DOCUMENTS

| EP | 1 380 642 A1 | 1/2004 |
| JP | 7-51065 B2 | 6/1995 |
| JP | 2832586 B2 | 10/1998 |
| JP | 11-127854 A | 5/1999 |
| JP | 2003-128691 A | 5/2003 |
| JP | 2003-204799 A | 7/2003 |
| WO | WO-03/033739 A1 | 4/2003 |
| WO | WO-2005/026347 A1 | 3/2005 |
| WO | WO-2005/037988 A2 | 4/2005 |
| WO | WO-2005/093052 A1 | 10/2005 |

OTHER PUBLICATIONS

Holodniy et al. Journal of Clinical Microbiology (1991), vol. 29, pp. 676-679.*
Sethu P et al., Anal Chem. 2004, vol. 76, No. 21, p. 6247-6253.

* cited by examiner

*Primary Examiner*—Patrick T Lewis
(74) *Attorney, Agent, or Firm*—Birch, Stewart, Kolasch & Birch, LLP.

(57) ABSTRACT

A method for separating and purifying RNA including the steps of passing a sample solution containing a nucleic acid, a washing solution and a recovering solution through a nucleic acid-adsorbing porous membrane to adsorb nucleic, adsorbing, washing and recovering, in which the nucleic acid adsorbing porous membrane is a porous membrane capable of adsorbing a nucleic acid by interaction involving substantially no ionic bond, and the sample solution is obtained by a process, comprising the steps of (I) injecting a test sample containing at least one of blood and leukocyte, and further containing an anticoagulant to a container, (II) adding a hemolytic agent to the container to obtain a leukocyte pellet, (III) adding a nucleic acid-solubilizing reagent to the leukocyte pallet to obtain a mixture solution and (IV) adding a water-soluble organic solvent to the mixture solution to obtain the sample solution containing the nucleic acid.

8 Claims, 1 Drawing Sheet

RNA  DNA

RNA  DNA

METHOD FOR SEPARATING AND PURIFYING RNA

TECHNICAL FIELD

The present invention relates to a method for separating and purifying RNA.

BACKGROUND ART

Various forms of nucleic acid are used in a variety of fields. For example, in the field of recombinant nucleic acid technology, nucleic acid is used in the form of probe, genomic nucleic acid and plasmid nucleic acid.

In the field of diagnostics, nucleic acid is used in various forms for various purposes. For example, a nucleic acid probe is routinely used in the detection and diagnosis of a human pathogen. Likewise, it is used for the detection of genetic disorders. It is also used for the detection of a food contaminant. Moreover, it is routinely used in locating, identifying and isolating nucleic acid of interest for a variety of reasons ranging from genetic mapping to cloning and recombinant expression.

In recent years, a method for identification of RNA expression has been developed such as Real-time PCR or microarray, and the correlation between RNA expression pattern and disorder, drug efficacy or the like has been examined with great importance.

In most cases, nucleic acid can be obtained only in an extremely small amount, and its separation and purification operations are complex and require time. These time-consuming complex operations are apt to cause loss of nucleic acid. RNA is very unstable, and thus can be easily degraded by heat, alkali and especially RNase. Therefore, it is very difficult to separate and purify highly pure RNA without having it degraded.

In purifying nucleic acid from samples obtained from serum, urine and bacterial cultures, there is an additional risk of contamination and false-positive result.

One of the well-known separation and purification methods comprises adsorption of nucleic acid on a solid phase such as silicon dioxide, silica polymer or magnesium silicate, and subsequent step such as washing or desorption (e.g., JP-B No. 7-51065 Patent Document 1). However, these methods involve problems of being not sufficient in simplicity, swiftness, and suitability for automation and reducing tool or apparatus size used in these methods, although high in isolation performance. The other problems come from the tools, apparatus and particularly adsorbents, including difficulty in production of an adsorbent of identical performance on an industrial scale, handling and realizing various shapes. Further, due to the fragility of a material and requiring a certain thickness or more to obtain mechanical strength, especially, in order to homogeneously interact DNase on a solid phase when degrading DNA with DNase for selectively recovering RNA from a mixture sample containing DNA and RNA, there are drawbacks such as requiring the DNase solution in a certain amount or more. DNase is relatively expensive, so that this could become a problem in case of selectively recovering RNA which necessity is predicted to increase much more in the future.

Further, one of the methods for separating and purifying nucleic acid simply and effectively is to use a solution for adsorbing nucleic acid onto a solid phase and a solution for desorbing nucleic acid from the solid phase membrane so that there is provided a method for separating and purifying nucleic acid by adsorbing and desorbing onto and from the solid phase comprising an organic polymer having a hydroxyl group on a surface thereof (JP-A No. 2003-128691 Patent Document 2). This method, however, needs further improvement.

Examples of other related known methods for separating and purifying nucleic acid include methods using centrifuge, magnetic beads and a filter. Further, an apparatus for separating and purifying nucleic acid, which use these methods, have been proposed. For example, an apparatus for separating and purifying nucleic acid using filter, wherein several filter tubes receiving filters are set on a rack, and therein a sample solution containing nucleic acid is injected where the bottom portion of the rack is applied with a sealing agent and sealed with an air chamber to reduce an inner pressure. Simultaneously the sample solution containing nucleic acid is sucked from the discharging side and passed through all filter tube, so as to adsorb nucleic acid onto the filter. Afterwards, a washing solution and a recovering solution are injected and again sucked thereto under reduced pressure so that washing and desorbing are also carried out. An automated apparatus using these procedures has been proposed. (e.g., Japanese Patent No. 2832586 Patent Document 3).

[Patent Document 1] JP-B No. 7-51065
[Patent Document 2] JP-A No. 2003-128691
[Patent Document 3] Japanese Patent No. 2832586

DISCLOSURE OF THE INVENTION

Meanwhile, the necessity of separating especially RNA in leukocyte is also increasing. About 100 times the number of erythrocyte compared with leukocyte is contained in blood. Furthermore, immature erythrocyte having RNA in erythrocyte, i.e., "reticulocyte", occupies about 1% of erythrocyte, thus it is about 10 times the number compared with leukocyte.

Since there are many reticulocyte, it is said that reticulocyte RNA occupies a maximum of 70% of the amount of RNA in whole blood. Therefore, when collecting RNA in leukocyte, RNA in reticulocyte becomes a noise, thus it is important to remove reticulocyte RNA beforehand.

A method of detecting nucleic acid in leukocyte solution obtained by lysing leukocyte after destructing erythrocyte is proposed (JP-W No. 8-501208). In this technique, CTAB or saponin is used as a hemolytic agent where hemolytic effect is verified, but since the direct nucleic acid detection reaction is performed without carrying out separation and purification of nucleic acid after dissolving leukocyte, it is considered as a method with very many noises. Especially in recent years, in the case of RNA which is important in its detection, an accurate result cannot be obtained if residues such as DNA and protein are not removed nearly completely. This technique is yet to come for carrying out the separation and purification of unstable RNA with high purity.

Moreover, in the case of separating and purifying RNA using a porous membrane, when a solution, which dissolved whole blood as it is without destructing erythrocyte, is used as a sample solution, the possibility of clogging is increased.

In order to avoid those two problems derived from erythrocyte, it is very important to destroy erythrocyte beforehand.

Therefore, it is an object of the invention to separate and purify RNA from leukocyte with good efficiency and high purity by destructing erythrocyte without destroying leukocyte.

The present inventors have made intensive studies to solve the above mentioned problems. As a result, they have found that, in the method for separating and purifying the nucleic acid, it is useful to include the steps of the following (1) to (3). Further, they have found that, in the method for separating and purifying the nucleic acid, by using the porous membrane capable of adsorbing the nucleic acid by interaction involving substantially no ionic bond, and by obtaining the leukocyte pellet in the process of preparing the sample solution before the steps of (1) to (3), it is possible to separate and purify RNA from the leukocyte at high yield, high purification. The invention has been accomplished based on these findings.

[1] A method for separating and purifying RNA comprising:

(1) passing a sample solution containing a nucleic acid through a nucleic acid-adsorbing porous membrane to adsorb the nucleic acid to the porous membrane;

(2) passing a washing solution through the nucleic acid-adsorbing porous membrane to wash the porous membrane while adsorbing the nucleic acid; and (3) passing a recovering solution through the nucleic acid-adsorbing porous membrane to desorb the nucleic acid from the porous membrane, wherein the nucleic acid adsorbing porous membrane is a porous membrane capable of adsorbing a nucleic acid by interaction involving substantially no ionic bond, and wherein the sample solution containing the nucleic acid is obtained by a process for preparing a sample solution, the process comprising:

(I) injecting a test sample containing: at least one of blood and leukocyte; and an anticoagulant to a container;

(II) adding a hemolytic agent to the container to obtain a leukocyte pellet;

(III) adding a nucleic acid-solubilizing reagent to the leukocyte pellet to obtain a mixture solution; and (IV) adding a water-soluble organic solvent to the mixture solution to obtain the sample solution containing the nucleic acid.

[2] The method for separating and purifying RNA as described in [1] above, wherein the hemolytic agent comprises at least one selected from ammonium chloride, sodium chloride, ammonium oxalate and saponin.

[3] The method for separating and purifying RNA as described in [1] or [2] above, wherein after adding the hemolytic agent in the step (II), an incubation is carried out at 0 to 35° C.

[4] The method for separating and purifying RNA as described in any one of [1] to [3] above, wherein the nucleic acid-solubilizing reagent comprises at least one selected from a chaotropic salt, a nucleic acid stabilizing agent, a surfactant, a buffering agent and a defoaming agent.

[5] The method for separating and purifying RNA as described in [4] above, wherein the chaotropic salt is a guanidinium salt.

[6] The method for separating and purifying RNA as described in [4] or [5] above, wherein the nucleic acid stabilizing agent is a reducing agent.

[7] The method for separating and purifying RNA as described in any one of [4] to [6] above, wherein the surfactant includes a nonionic surfactant.

[8] The method for separating and purifying RNA as described in any one of [1] to [7] above, wherein at least one of the sample solution containing the nucleic acid, the washing solution and the recovering solution is passed through the nucleic acid-adsorbing porous membrane under a pressurizing condition.

[9] An apparatus for automatically carrying out a method for separating and purifying RNA as described in any one of [1] to [8] above.

[10] A kit for carrying out a method for separating and purifying RNA as described in any one of [1] to [8] above, the kit comprising:

(i) a cartridge for separation and purification of nucleic acid receiving a nucleic acid-adsorbing porous membrane; and reagents comprising;

(ii) a hemolytic agent;

(iii) a nucleic acid-solubilizing reagent;

(iv) a washing solution; and (v) a recovering solution.

[11] An apparatus for automatically carrying out use of a kit as described in [10] above.

1. A method for separating and purifying RNA, comprising the steps of:

(1) passing a sample solution containing a nucleic acid though a nucleic acid-adsorbing porous membrane to adsorb nucleic acid to the porous membrane;

(2) passing a washing solution through the nucleic acid-adsorbing porous membrane to wash the porous membrane while adsorbing the nucleic acid; and (3) passing the recovering solution through the nucleic acid-adsorbing porous membrane to desorb the nucleic acid from the porous membrane, wherein the nucleic acid adsorbing porous membrane is a porous membrane capable of adsorbing the nucleic acid by interaction involving substantially no ionic bond, and wherein the sample solution containing the nucleic acid is obtained by a process for preparing the sample solution, comprising the steps of:

(I) injecting a test sample containing either of blood and leukocyte, and further containing an anticoagulant to a container;

(II) adding a hemolytic agent to the container to obtain a leukocyte pellet;

(III) adding a nucleic acid-solubilizing reagent to the leukocyte pellet to obtain a mixture solution; and (IV) adding a water-soluble organic solvent to the mixture solution to obtain the sample solution containing the nucleic acid.

2. The method for separating and purifying RNA as described in 1, wherein the hemolytic agent contains at least one selected from ammonium chloride, sodium chloride, ammonium oxalate and saponin.

3. The method for separating and purifying RNA as described in 1 or 2, wherein after adding the hemolytic agent in step (II), the incubation is carried out at 0 to 35° C.

4. The method for separating and purifying RNA as described in any one of 1 to 3, wherein the nucleic acid-solubilizing reagent contains at least one selected from a chaotropic salt, a nucleic acid stabilizing agent, a surfactant, a buffering agent and a defoaming agent.

5. The method for separating and purifying RNA as described in 4, wherein the chaotropic salt is a guanidinium salt.

6. The method for separating and purifying RNA as described in 4 or 5, wherein the nucleic acid stabilizing agent is a reducing agent.

7. The method for separating and purifying RNA as described in any one of 4 to 6, wherein the surfactant includes a nonionic surfactant.

8. The method for separating and purifying RNA as described in any one of 1 to 7, wherein any one of the sample solution containing the nucleic acid, the washing solution and the recovering solution is passed through the nucleic acid-adsorbing porous membrane under a pressurizing condition.

9. An apparatus for automatically carrying out the method for separating and purifying RNA as described in any one of 1 to 8.

10. A kit for carrying out the method for separating and purifying RNA as described in any one of 1 to 9, comprising (i) a cartridge for separation and purification of nucleic acid adopting the nucleic acid-adsorbing porous membrane, and reagents including (ii) a hemolytic agent, (iii) a nucleic acid-solubilizing reagent, (iv) a washing solution and (v) a recovering solution.

11. An apparatus for automatically carrying out the use of the kit as described in 10.

BRIEF DESCRIPTION OF THE DRAWING

FIG. 1 is a diagram of a photograph obtained by subjecting RNA, which was separated and purified according to the method of the invention, to agarose gel (TAE migration buffer) electrophoresis; and.

Figure 1:
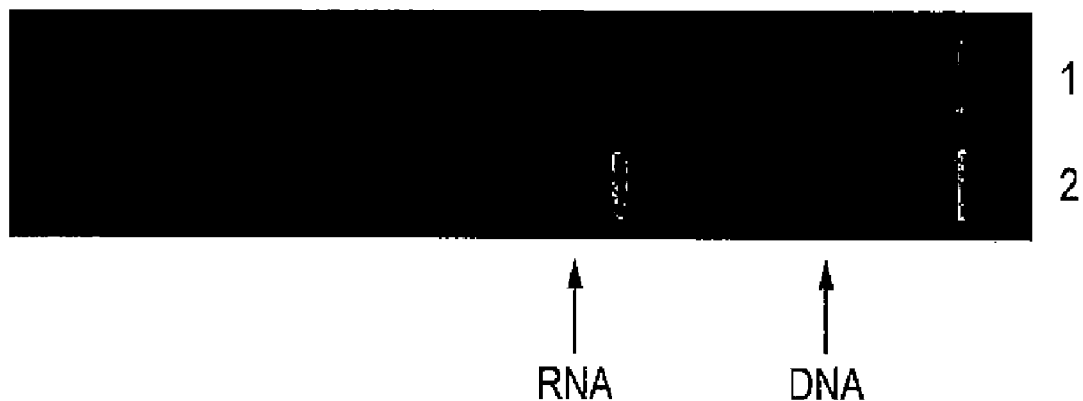

2: denotes RNA obtained from human whole blood having total white blood cell number of $1 \times 10^7$;

3: denotes 1 kb PLUS Ladder (Invitrogen Corporation); and

4, and 5: denote RNA obtained from human whole blood having total white blood cell number of $1 \times 10^7$.

BEST MODE FOR CARRYING OUT THE INVENTION

The method of the present invention for separation and purification of RNA at least comprises the following steps, (1) a step of passing a sample solution containing a nucleic acid though a nucleic acid-adsorbing porous membrane to adsorb nucleic acid to the porous membrane (hereinafter, referred to as "adsorbing step");

(2) a step of passing a washing solution through the nucleic acid-adsorbing porous membrane to wash the porous membrane while adsorbing the nucleic acid (hereinafter, referred to as "washing step"); and (3) a step of passing the recovering solution through the nucleic acid-adsorbing porous membrane to desorb the nucleic acid from the porous membrane (hereinafter, referred to as "recovering step").

Preferably, in each of the steps (1), (2) and (3), the sample solution containing nucleic acids, the washing solution and the recovering solution are passed through the nucleic acid-adsorbing porous membrane under pressurized condition. More preferably, in each of the steps (1), (2) and (3), a sample solution containing nucleic acid, a washing solution or a recovering solution are injected into one opening of a cartridge for separation and purification of nucleic acid comprising a container having at least two openings wherein the cartridge for separation and purification of nucleic acid receives the nucleic acid-adsorbing porous membrane in an inside of the container, and make an inside of the cartridge into a pressurized state by using a pressure difference-generating apparatus connected to the one opening of the cartridge, so as to pass each injected solutions through the nucleic acid-adsorbing porous membrane and discharge them from an another opening. The apparatus can be automated in a compact form by passing the sample solution containing nucleic acids, the washing solution and the recovering solution through the porous membrane under pressurized condition, which is preferred. The pressure to be applied is preferably about 10 to 300 kpa, and more preferably about 40 to 200 kpa.

In the steps (1) to (3) described above, the procedures from the first step of injection of a sample solution containing nucleic acids to the step of obtaining RNA outside the cartridge for separation and purification of nucleic acids can be completed within 20 minutes or, under preferred conditions, within 2 minutes. Moreover, the above-described steps for separation and purification of nucleic acid enables one to obtain nucleic acids in a yield of 50% by weightmass or more or, under preferred conditions, 90% by weightmass or more, based on the amount of the whole nucleic acids contained in the test sample. (In this specification, mass ratio is equal to weight ratio.)

Further, the above-described steps for separation and purification of RNA enable one to recover RNA having a purity of 1.8 to 2.2, in terms of values measured by means of a spectrophotometer for UV light to visible light (260 nm/280 nm). Thus, RNA with less contamination and high purity can constantly be obtained. Under preferred conditions, RNA having a high purity of approximately 2.0 in the value measured by means of the spectrophotometer for UV light to visible light (260 nm/280 nm) can be recovered.

Examples of the pressure difference-generating apparatus used in the above-described steps include a syringe, a pipette, an increased pressure-generating pump such as a perista pump, and a reduced pressure generator such as an evaporator. Among these, a syringe is appropriate for manual operation, and a pump is appropriate for automated operation.

Also, a pipette has the advantage that it can be operated in one-hand. Preferably, the pressure difference-generating apparatus is detachably connected to one opening of the cartridge for separation and purification of nucleic acids.

The sample solution of the present invention obtained by the process of preparing the sample solution at least comprises the following steps, (I) a step of injecting a test sample containing either of blood and leukocyte, and further containing an anticoagulant into a container;

(II) a step of adding a hemolytic agent to the container to obtain a leukocyte pellet;

(III) a step of adding a nucleic acid-solubilizing reagent to the leukocyte pellet to obtain a mixture solution; and (IV) a step of adding a water-soluble organic solvent to the mixture solution obtained in (III) to obtain the sample solution containing the nucleic acid.

According to the steps described above, erythrocyte is destructed without having leukocyte destroyed, thus to obtain the leukocyte pellet. Further, by dissolving the cell membrane and the nuclear membrane of leukocyte, the sample solution containing nucleic acids having nucleic acids dispersed in the aqueous solution can be obtained.

In order to dissolve the cell membrane and the nuclear membrane of leukocyte effectively, it is important that erythrocyte is preliminarily destructed and removed. Having erythrocyte readily removed is important in the prevention of clogging.

Dissolution of the cell membrane and the nuclear membrane of leukocyte are necessary and important for solubilizing the nucleic acid, and particularly RNA, which is to be extracted.

(I) Step of Injecting a Test Sample Containing Either of Blood and Leukocyte, and Further Containing an Anticoagulant into a Container In the invention, the test sample contains either of blood and leukocyte. Examples of blood include whole blood. Further, the leukocyte encompasses those obtained from the whole blood.

The test sample in the invention further contains an anticoagulant. Examples of the anticoagulant include, in general, EDTA, herapin, sodium citrate, sodium fluoride, ACD (acid citrate dextrose solution) and the like, and they may be used alone or in combination of two or more. The content of the anticoagulant may be in the range of its typical use amount. The invention is not limited to these anticoagulants, but the separation and purification of RNA can be carried out efficiently according to the method for separation and purification of RNA comprising the steps of (1) to (3) above, irrespective of the type of anticoagulant contained in the test sample.

The sample solution containing nucleic acids may contain a single type of nucleic acid or two or more different types of nucleic acids. The number of test samples may be one or in a plural (parallel operation of a plurality of the test samples using a plurality of containers). The length of nucleic acids to be recovered is not limited, but, for example, an arbitrary length in the range of several bps to several Mbps can be used. However, the length of nucleic acids are generally in a range from about several bps to about several hundreds kbps in the viewpoint of easy handling. The nucleic acid separation and purification method of the invention can swiftly recover longer nucleic acid compared with a conventional simple method. The length of nucleic acids to be recovered by the invention is preferably 50 kbps or longer, more preferably 70 kbps or longer, and still more preferably 100 kbps or longer.

As a container for injecting the test sample, though not limited, a plastic tube, a glass vial, a test tube or the like is preferred. These containers which are nuclease-free and pyrogen-free are more preferred.

As an injection method when injecting the test sample into the container, though not limited, laboratory apparatus such as a pipette or a dropper is preferably used. These apparatus which are nuclease-free and pyrogen-free are more preferred.

Injection to the container is not particularly limited, but any method or apparatus can be used.

(II) Step of Adding a Hemolytic Agent to the Container to Obtain a Leukocyte Pellet In the invention, a hemolytic agent is added to obtain a leukocyte pellet. According to this step, erythrocyte can be destructed without destroying leukocyte, and the leukocyte pellet can be mainly obtained.

Examples of hemolytic agents include ammonium chloride, sodium chloride, ammonium oxalate and saponin. Using a hemolytic agent containing at least one selected therefrom, erythrocyte is destructed without destroying leukocyte, which is preferable. Particularly, using a hemolytic agent containing ammonium chloride is preferred. The optimal concentration of a hemolytic agent is different depending on the hemolytic agent, but it is preferably in the range of from 0.1 to 20%. In the case of ammonium chloride, it is preferably in the range of from 0.8 to 1.0%.

The liquid amount of a hemolytic agent, in the case of whole blood, is preferably in the ratio of whole blood: hemolytic agent=1:2 to 20, and more preferably 1:4 to 10.

In addition, it is preferable to carry out the incubation at 0 to 35° C. after adding the hemolytic agent. The incubation is preferably carried out for 1 to 30 minutes, and more preferably for 5 to 20 minutes.

When adding a hemolytic agent to whole blood, after completion of destructing erythrocyte, the turbid solution becomes transparent. After such a state has occurred, the solution is centrifuged at 300×g to 3000×g, and the leukocyte pellet can be obtained.

(III) Step of Adding a Nucleic Acid-Solubilizing Reagent to the Leukocyte Pellet to Obtain a Mixture Solution In the invention, a nucleic acid-solubilizing reagent is used to dissolve the cell membrane of leukocyte and nuclear membrane and solubilize nucleic acids. As a nucleic acid-solubilizing reagent, a reagent containing at least one selected from a chaotropic salt, a nucleic acid-stabilizing agent, a surfactant, a buffer and a defoaming agent is preferably used. The nucleic acid-solubilizing reagent may be in solution or in dried substance, but using it in solution is preferred. Further, the nucleic acid-solubilizing reagent may contain components other than a chaotropic salt, a nucleic acid-stabilizing agent, a surfactant, a buffer and a defoaming agent.

As the chaotropic salt, known chaotropic salts can be used without any particular limitations. Examples of chaotropic salt include guanidine salt, sodium isothiocyanate, sodium iodide and potassium iodide. Among these, guanidine salt is preferred in the viewpoint of inhibiting RNase. Examples of guanidine salt include guanidine hydrochloride, guanidine isothiocyanate and guanidine thiocyanate salt (guanidine thiocyanate), and among these guanidine hydrochloride or guanidine thiocyanate salt is preferred. These salts can be used alone or in combination of two or more.

The concentration of a chaotropic salt in the nucleic acid-solubilizing reagent is preferably 0.5 mol/L or more, more preferably from 0.5 to 8 mol/L and even more preferably from 1 to 6 mol/L.

It is possible to use a chaotropic substance such as urea instead of a chaotropic salt.

The nucleic acid-solubilizing reagent preferably contains a nucleic acid stabilizing agent. The nucleic acid stabilizing agent can be used for stabilizing nucleic acid in a test sample, which is preferable. More preferably, any one or more selected from a chaotropic salt, a surfactant, a buffer and a defoaming agent is coexisted. In this regard, a recovering yield and a recovering efficiency of finally obtained RNA are improved so that the minimization and acceleration of a test sample are enabled, thus preferred.

As the nucleic acid stabilizing agent, one having a reaction to inactivate a nuclease activity can be mentioned. Depending on a test sample, there are cases where nuclease, which degrades nucleic acid, is comprised thereto so that when nucleic acid is homogenized, nuclease reacts with the nucleic acid, so as to result in a remarkable reduction of a yield amount.

As a stabilizing agent having a function to inactivate nuclease activity, a compound used as a typical reducing agent can be used. Examples of the reducing agent include hydrogenated compounds such as hydrogen, hydrogen iodide, hydrogen sulfide, aluminum lithium hydride and sodium borohydride; a highly electropositive metal such as alkaline metal, magnesium, calcium, aluminum and zinc, or amalgam thereof; organic oxides such as aldhydes, sugars, formic acid and oxalic acid; and mercapto compounds. Among these, the mercapto compounds are preferred.

Examples of mercapto compounds include N-acetyl cysteine, mercapto ethanol, alkyl mercaptane and the like. The mercapto compounds can be used alone or in combination of two or more.

The concentration of the nucleic acid stabilizing agent in the nucleic acid-solubilizing reagent is preferably from 0.1 to 20% by weightmass, and more preferably from 0.3 to 15% by weightmass. The concentration of the mercapto compounds in the nucleic acid-solubilizing reagent is preferably from 0.1 to 20% by weightmass, and more preferably from 0.5 to 15% by weightmass.

Examples of Surfactants include a nonionic surfactant, a cationic surfactant, an anionic surfactant, an amphoteric surfactant.

In the invention, the nonionic surfactant and the cationic surfactant can be preferably used. The nonionic surfactant is particularly preferable because it may change the polarity of environment more desirably.

Examples of the nonionic surfactants include a polyoxyethylene alkyl phenyl ether-based surfactant, a polyoxyethylene alkyl ether-based surfactant and fatty acid alkanolamide, and preferably a polyoxyethylene allyl ether-based surfactant. Examples of the polyoxyethylene (POE) alkyl ether surfactant include POE decyl ether, POE lauryl ether, POE tridecyl ether, POE alkylene decyl ether, POE sorbitan monolaurate, POE sorbitan monooleate, POE sorbitan monostearate, tetraoleic polyoxyethylene sorbit, POE alkyl amine and POE acetylene glycol.

Examples of cationic surfactants include cetyl trimethyl ammonium bromide, dodecyl trimethyl ammonium chloride, tetradecyl trimethyl ammonium chloride, cetyl pyridinium chloride.

These surfactants can be used alone or in combination of two or more. The concentration of the surfactant in the nucleic acid-solubilizing reagent is preferably from 0.1 to 20% by weightmass.

The nucleic acid-solubilizing reagent having preferably pH of 3 to 8, more preferably pH of 4 to 7, and further preferably pH of 5 to 7, is used.

As the buffer, a normal pH buffer (buffer) can be mentioned, and preferably, a biochemical pH buffer can be mentioned. Examples of such buffers include buffers containing citrate, phosphate or acetate, Tris-HCl, TE (Tris-HCl/EDTA), TBE (Tris-Borate/EDTA), TAE (Tris-Acetate/EDTA) and a GUD buffer. Examples of the GUD buffer include MES (2-Morpholinoethanesulfonic acid), Bis-Tris(Bis(2-hydroroxyethyl) iminotris(hydroxymethyl)methane), HEPES (2-[4-(2-Hydroxyethyl)-1-piperazinyl]ethanesulfonic acid), PIPES (Piperaxine-1,4-bis(2-ethanesulfonic acid)), ACES (N-(2-Acetamino)-2-aminoethanesulfonic acid), CAPS(N-Cyclohexyl-3-aminopropanesulfonic acid), TES (N-Tris(hydroxymethyl)methyl-2-aminoethanesulfonic acid).

The concentration of these buffers in the nucleic acid-solubilizing reagent is preferably from 1 to 500 mmol/L.

Examples of defoaming agents include a silicon-based defoaming agent (e.g., silicon oil, dimethyl polysiloxane, silicon emulsion, denatured polysiloxane, silicon compound, etc.), an alcohol-based defoaming agent (e.g., acetylene glycol, heptanol, ethyl exanol, higher alcohol, polyoxy alkylene glycol, etc.), an ether-based defoaming agent (e.g., heptyl cellosolve, nonyl cellosolve-3-heptylcorbitol, etc.), a fatty oil-based defoaming agent (e.g., animal and plant fat, etc.), a fatty acid-based defoaming agent (e.g., stearic acid, oleic acid, palmitic acid, etc.), a metallic soap-based defoaming agent (e.g., aluminum stearate, calcium stearate, etc.), a fatty acid ester-based defoaming agent (e.g., a natural wax, tributyl phosphate, etc.), a phosphate ester-based defoaming agent (e.g., sodium octyl phosphate, etc.), an amine-based defoaming agent (e.g., diamyl amine, etc.), an amide-based defoaming agent (e.g., amide stearate, etc.) and other defoaming agents (e.g., ferric sulfate, bauxite, etc.), and the like. These defoaming agents may be used alone or in combination of two or more. Two compounds combined from silicon-based and alcohol-based defoaming agents are particularly preferred.

The concentration of a defoaming agent in nucleic acid-solubilizing reagent is preferably from 0.1 to 10% by weightmass.

In addition, the nucleic acid-solubilizing reagent may contain water-soluble organic solvents. Examples of the water-soluble organic solvent include acetone, alcohols, dimethylformamide and the like. The purpose of the water-soluble organic solvent is to increase the solubility of various reagents contained in the nucleic acid-solubilizing reagent, which is preferable. Among these, alcohols are preferred. As for alcohols, any one of primary, secondary, tertiary alcohols can be used. More preferably, methanol, ethanol, propanol and its isomer, butanol and its isomer can be used. These water-soluble organic solvents may be used alone or in combination of two or more. The concentration of these water-soluble organic solvents in the nucleic acid-solubilizing reagent is preferably from 1 to 20% by weightmass.

It is desirable to treat leukocyte with 50 to 1000 μl of the nucleic acid-solubilizing reagent based on 10 to $1 \times 10^9$ of leukocyte. The liquid amount of the nucleic acid-solubilizing reagent can be varied in the range where leukocyte is dissolved and the volume of the cartridge is not exceeded.

A method for mixing leukocyte and the nucleic acid-solubilizing reagent is not particularly limited. For example, when mixing, using an agitating apparatus at 30 to 3000 rpm for 1 second to 3 minutes is preferred. By this mixing, the final yield of separated and purified RNA can be increased desirably. On the other hand, rollover-mixing for 5 to 30 times is also preferred. In addition, pipetting operation for 10 to 50 times enables blending, and in this case the final yield of separated and purified RNA can be increased in a simple operation, thus preferred.

It is preferable to perform the homogenizing treatment on the mixture solution obtained by adding the nucleic acid-solubilizing reagent to leukocyte. By performing the homogenizing treatment, the optimum for automated treatment is improved, which is preferable. As the homogenizing treatment, for example, an ultrasonic treatment, a treatment using a sharp prong, a treatment using high-speed stirring, an extrusion treatment from a fine space, a treatment using beads such as glass, stainless steel, zirconia and the like can be performed. For performing these treatments, though not particularly limited, any one of, for example, mixers such as Vortex, homogenizers of Rotor-Stator type, Potter type, Dounce type or the like, or commercially available homogenizers such as a beads-mill, a pestle, a French press, a grinder, a blade homogenizer can be used. When performing homogenizing treatment before adding the nucleic acid-solubilizing reagent, it is possible to perform the treatment by freezing the test sample with liquid nitrogen, and then using a beads-mill or crusher-mill, a mortar, a grinder or the like.

(IV) Step of Adding a Water-Soluble Organic Solvent to the Mixture Solution Obtained in (III) to Obtain a Sample Solution Containing Nucleic Acids.

As the water-soluble organic solvent, an alcohol-based compound is preferably used, although not limited thereto. For alcohol-based compounds, any one of primary, secondary, tertiary alcohols can be used, and methanol, ethanol, propanol and its isomer, butanol and its isomer can preferably be used. These water-soluble organic solvents may be used alone or in combination of two or more. The final concentration of these water-soluble organic solvents in the sample solution containing nucleic acids (hereinafter, referred to as nucleic acid-mixture solution) is preferably from 5 to 90% by weightmass, more preferably from 15 to 75% by weightmass, and further preferably 15 to 50% by weightmass. By employing the optimal concentration of EtOH, RNA can be separated and purified with good efficiency and high purity by reducing the contamination of genome DNA to the recovered sample even without using a DNase. When mixing after adding a water-soluble organic solvent, using an agitating apparatus at 30 to 3000 rpm for 1 second to 3 minutes is preferred. By this mixing, the final yield of separated and purified RNA can be increased. Furthermore, mixing by inverting the tube for 5 to 30 times is also preferred. In addition, pipetting operation for 10 to 50 times also enables blending of the mixture.

In addition, the obtained nucleic acid-mixture solution having surface tension of 0.05 $J/m^2$ or less, and having viscosity of 1 to 10000 mPa, and further having specific gravity in a range of 0.8 to 1.2 is preferred. By using a solution fit in these ranges, removing the mixture solution of nucleic acid waste after passing the mixture solution of nucleic acid through a nucleic acid-adsorbing porous membrane is easily carried out.

(1) Step of Passing a Sample Solution Containing a Nucleic Acid Though a Nucleic Acid-Adsorbing Porous Membrane to Adsorb Nucleic Acid to the Porous Membrane (Adsorbing Step)

(1) A nucleic acid-adsorbing porous membrane and the step of adsorbing nucleic acid to the nucleic acid-adsorbing porous membrane used in the invention will be described below.

The nucleic acid-adsorbing porous membrane of the invention capable of passing through a solution internally, is used. Herein, "capable of passing through a solution internally" means that when a space contacting one side and a space contacting the other side of a membrane has a different pressure, a solution is enabled to pass through the membrane from the high pressured space to the low pressured space. On the other hand, it means that when the centrifuge force is applied to the membrane, a solution is enabled to pass through the membrane in the direction of the centrifuge force.

The nucleic acid-adsorbing porous membrane of the invention adsorbs nucleic acid by interaction therebetween, in which an ionic bond is not substantially involved. It means that "ionization" is not occurred under conditions of using a porous membrane, and it is assumed that nucleic acid and the porous membrane are attracting therebetween by changing the polarity of the environment. As a result, the nucleic acid-adsorbing porous membrane is excellent in separation ability and good in washing efficiency and preferably enables isolation and purification of nucleic acid, which is preferable. More preferably, the nucleic acid-adsorbing porous membrane is a porous membrane having a hydrophilic group, and it is assumed that the hydrophilic groups of nucleic acid and a porous membrane are attracting therebetween by changing the polarity of environment.

Herein, the hydrophilic group represents a polar group (an atomic group) which can have interaction therebetween with water, and all groups (atomic groups) related to adsorbing nucleic acid are suitable. For a hydrophilic group, the intensity of interaction therebetween with water having about intermediate intensity (see the page with the term "a hydrophilic group" as "a group which the hydrophilicity is not very strong", Dictionary of Chemistry, published by Kyoritsu Shuppan Co., Ltd.) is suitable. Examples thereof include a hydroxyl group, a carboxyl group, a cyano group, and an oxyethylene group and the like. A hydroxyl group is preferred.

Herein, a porous membrane having a hydrophilic group means that the material itself composing the porous membrane is having a hydrophilic group, or a hydrophilic group is introduced to the porous membrane by treating or coating the material which composes the porous membrane. Any one of organic or inorganic materials is suitable for the material composing the porous membrane. For example, the porous membrane, in which the material itself for composing the porous membrane is an organic material having a hydrophilic group; in which the hydrophilic group is introduced thereto by treating the organic material not having a hydrophilic group which composes the porous membrane; in which the hydrophilic group is introduced thereto by coating the organic material not having a hydrophilic group which composes the porous membrane; in which the material itself for composing the porous membrane is an inorganic material having a hydrophilic group; in which the hydrophilic group is introduced thereto by treating the inorganic material not having a hydrophilic group which composes the porous membrane; in which the hydrophilic group is introduced thereto by coating the inorganic material not having a hydrophilic group which composes the porous membrane can be used. However, for simplicity in processing, using an organic material such as organic polymer for the material composing the porous membrane is preferred.

Examples of the porous membrane of a material having a hydrophilic group include polyhydroxy ethylacrylate, polyhydroxyl ethylmethacrylate, polyvinyl alcohol, polyvinyl pyrrolidone, polyacrylic acid, polymethacrylic acid, polyoxyethylene, acetyl cellulose, and a mixture of acetyl celluloses different from each other in acetyl value, and the like are suitable for composing the porous membrane, but particularly a porous membrane comprising organic material having a hydroxyl group, particularly a porous membrane comprising the organic polymer having a hydroxyl group can be used preferably.

For a porous membrane of an organic material having a hydroxyl group, a material having polysaccharide structure is preferred, and an organic polymer in a porous membrane composed of a mixture of acetyl celluloses different from each other in acetyl value, can be used more preferably. Examples of the mixture of acetyl celluloses different from each other in acetyl value include a mixture of triacetyl cellulose and diacetyl cellulose, a mixture of triacetyl cellulose and monoacetyl cellulose, a mixture of triacetyl cellulose, diacetyl cellulose and monoacetyl cellulose and a mixture of diacetyl cellulose and monoacetyl cellulose can be used preferably. Particularly preferably, a mixture of triacetyl cellulose and diacetyl cellulose can be used. The mixing ratio (mass ratio) of triacetyl cellulose and diacetyl cellulose is preferably from 99:1 to 1:99, and more preferably from 90:10 to 50:50.

More preferable organic material having a hydroxyl group is a saponification of acetyl cellulose described in JP-A No. 2003-128691. Saponification of acetyl cellulose used herein means that a mixture of acetyl celluloses different from each other in acetyl value is treated with saponification, and examples thereof including saponification of a mixture of triacetyl cellulose and diacetyl cellulose, a mixture of triacetyl cellulose and monoacetyl cellulose, a mixture of triacetyl cellulose, diacetyl cellulose and monoacetyl cellulose, and a mixture of diacetyl cellulose and monoacetyl cellulose can be used preferably. More preferably, a saponification of a mixture of triacetyl cellulose and diacetyl cellulose can be used. The mixing ratio (mass ratio) of triacetyl cellulose and diacetyl cellulose is preferably from 99:1 to 1:99, and more preferably from 90:10 to 50:50. In this case, the amount of hydroxyl group (density) on the surface of the porous membrane is controlled in accordance to the degree of surface saponification treatment (surface saponification degree).

In order to increase the efficacy of nucleic acid separation, it is preferred to have more amount (density) of the hydroxyl group on a surface of the porous membrane. The saponification degree (surface saponification degree) of an organic material obtained from saponification is preferably 5 or more and 100% or less, and more preferably 10 or more and 100% or less.

In addition, in order to enlarge the surface area of the organic polymers having a hydroxyl group on their surface, the treatment of surface saponification of acetyl cellulose is preferred.

A porous membrane having a front surface and a back surface symmetrical to each other is suitable, but a porous membrane having a front surface and a back surface asymmetrical to each other can be used preferably.

Herein, the saponification treatment means that acetyl cellulose comes in contact with saponification treatment solution (e.g., sodium hydroxide solution). As a result, the saponification treatment solution contacted ester group of ester derivative of acetyl cellulose is hydrolyzed, and a hydroxyl group is introduced to form regenerated cellulose. Thereby the prepared regenerated cellulose is different in crystalline form from the original cellulose. In order to change the saponification degree, saponification treatment is carried out having changed the concentration or treating time of sodium hydroxide. The saponification degree can be easily determined by means of NMR (e.g., detecting a degree of reduction in the peak of carbonyl group).

A method for introducing a hydroxyl group to a porous membrane containing organic material not having a hydroxyl group is to bond a graft polymer chain having a hydroxyl group in an inner polymer chain or a side chain to a porous membrane. A method for bonding a graft polymer chain to an organic material of a porous membrane include two methods such as a method for chemically bonding a porous membrane with a graft polymer chain and a method for polymerizing a compound having a double bond capable of polymerization using a porous membrane as a starter to form graft polymer chain.

Firstly, in the method of chemically bonding a porous membrane and graft polymer chain, a polymer having a functional group capable of reacting with the porous membrane in the terminus or side chain of the polymer is used, and they are grafted through a chemical reaction of this functional group with a functional group of the porous membrane. The functional group capable of reacting with the porous membrane is not particularly limited as long as it can react with a functional group of the porous membrane. Examples thereof include a silane coupling group such as alkoxysilane, an isocyanate group, an amino group, a hydroxyl group, a carboxyl group, a sulfonate group, a phosphate group, an epoxy group, an allyl group, a methacryloyl group, an acryloyl group and the like. Examples of the compound particularly useful as the polymer having a reactive functional group in the terminus or side chain of the polymer include a polymer having a trialkoxysilyl group in the polymer terminus, a polymer having an amino group in the polymer terminus, a polymer having a carboxyl group in the polymer terminus, a polymer having an epoxy group in the polymer terminus and a polymer having an isocyanate group in the polymer terminus. The polymer to be used herein is not particularly limited as long as it has a hydrophilic group which is concerned in the adsorption of nucleic acid, and specific examples thereof include polyhydroxyethyl acrylic acid, polyhydroxyethyl methacrylic acid and salts thereof, polyvinyl alcohol, polyvinyl pyrrolidone, polyacrylic acid, polymethacrylic acid and salts thereof, polyoxyethylene and the like.

The method in which a compound having a polymerizable double bond is made into a graft polymer chain by polymerizing it using the porous membrane as the starting point is generally called surface graft polymerization. The surface graft polymerization method means a method in which an active species is provided on a porous membrane surface by plasma irradiation, light irradiation, heating or the like method, and a polymerizable compound having double bond arranged in contact with the porous membrane is linked to the porous membrane by polymerization. It is necessary that the compound useful for forming a graft polymer chain linked to the porous membrane has both of two characteristics of having a polymerizable double bond and having a hydrophilic group which is concerned in the adsorption of nucleic acid. As such a compound, any one of the polymers, oligomers and monomers having a hydrophilic group can be used provide that it has a double bond in the molecule. Particularly useful compound is a monomer having a hydrophilic group. Specific examples of the particularly useful monomer having a hydrophilic group include the following monomers. For example, hydroxyl group-containing monomers such as 2-hydroxyethyl acrylate, 2-hydroxyethyl methacrylate, glycerol monomethacrylate and the like, can be used particularly suitably. In addition, carboxyl group-containing monomers such as, acrylic acid, methacrylic acid and the like or alkali metal salts and amine salts thereof can also be used suitably.

As another method for introducing a hydrophilic group into a porous membrane of an organic material having no hydrophilic group, a material having a hydrophilic group can be coated. The material to be used in the coating is not particularly limited as long as it has a hydrophilic group which is concerned in the adsorption of nucleic acid, but is preferably a polymer of an organic material from the viewpoint of easy handling. Examples of the polymer include polyhydroxyethyl acrylate, polyhydroxyethyl methacrylate and salts thereof, polyvinyl alcohol, polyvinyl pyrrolidone, polyacrylic acid, polymethacrylic acid and salts thereof, polyoxyethylene, acetyl cellulose, a mixture of acetyl celluloses different from each other in acetyl value and the like, but a polymer having a polysaccharide structure is preferred.

Further, it is possible to coat acetyl cellulose or a mixture of acetyl celluloses different from each other in acetyl value on a porous membrane of an organic material having no hydrophilic group and then to subject the coated acetyl cellulose or a mixture of acetyl celluloses different from each other in acetyl value to a saponification treatment. In this case, the saponification ratio is preferably 5% or more and 100% or less, and the saponification ratio is more preferably 10% or more and 100% or less.

As the porous membrane of an inorganic material having a hydrophilic group, a porous membrane containing a silica compound can be mentioned. As the porous membrane containing a silica compound, a glass filter can be mentioned. Also, a porous silica thin membrane as described in Japanese Patent No. 30583442, can be mentioned. This porous silica thin membrane can be prepared by spreading a developing solution of a cationic amphipathic substance having an ability to form a bimolecular membrane on a base material, preparing multi-layered bimolecular thin membranes of the amphipathic substance by removing the solvent from the liquid membrane on the base material, allowing the multi-layered bimolecular thin membranes to contact with a solution containing a silica compound, and then extracting and removing the aforementioned multi-layered bimolecular thin membranes.

As the method for introducing a hydrophilic group into a porous membrane of an inorganic material having no hydrophilic group, there are two methods including a method in which the porous membrane and a graft polymer chain are chemically bonded and a method in which a graft polymer chain is polymerized using a hydrophilic group-containing monomer having a double bond in the molecule, using the porous membrane as the starting point.

When the porous membrane and graft polymer chain having a hydrophilic group are chemically bonded, a functional group capable of reacting with a terminal functional group of the graft polymer chain is introduced into an inorganic material, and the graft polymer chain is chemically bonded thereto. Also, when a graft polymer chain is polymerized using a hydrophilic group-containing monomer having a double bond in the molecule and using the porous membrane as the starting point, a functional group which becomes the starting point in polymerizing the double bond-containing compound is introduced into the inorganic material.

As the graft polymer having a hydrophilic group and a hydrophilic group-containing monomer having a double bond in the molecule, the above-described graft polymer having a hydrophilic group and a hydrophilic group-containing monomer having a double bond in the molecule, described in the above, regarding the method for introducing a hydrophilic group into a porous membrane of an organic material having no hydrophilic group, can be suitably use.

Another method for introducing a hydrophilic group to a porous membrane of inorganic material not having a hydrophilic group is to coat a material having a hydrophilic group thereon. Materials used in coating are not particularly limited as long as the hydrophilic group participates in the adsorption of nucleic acid, but for easy workability, a polymer of an organic material is preferred. Examples of the polymer include polyhydroxyethyl acrylate, polyhydroxyethyl methacrylate and salts thereof, polyvinyl alcohol, polyvinyl pyrrolidone, polyacrylic acid, polymethacrylic acid and salts thereof, polyoxyethylene, acetyl cellulose, a mixture of acetyl celluloses different from each other in acetyl value and the like.

To the porous membrane of inorganic material not having a hydrophilic group, acetyl cellulose or a mixture of acetyl celluloses different from each other in acetyl value is coated thereon, and the coated acetyl cellulose or a mixture of acetyl celluloses different from each other in acetyl value can be subjected to saponification treatment. In this case, the saponification degree is preferably 5% or more and 100% or less, and more preferably about 10% or more and 100% or less.

Examples of the porous membrane of inorganic material not having a hydrophilic group include metals such as aluminum, ceramics such as glass, cement, pottery, or a porous membrane fabricated by processing new ceramics, silicon, active charcoal, and the like.

The nucleic acid-adsorbing porous membrane is capable of passing through a solution internally, and has the thickness thereof is preferably from 10 to 500 μm. More preferable thickness is from 50 to 250 μm. The thickness being thinner is more preferable in the viewpoint of easy washing.

The nucleic acid-adsorbing porous membrane capable of passing through a solution internally has the minimum pore size of preferably 0.22 μm or more. More preferable minimum pore size is 0.5 μm or more. In addition, using a porous membrane having the ratio of the maximum pore size and the minimum pore size to be 2 or more is preferred. As a result, a sufficient surface area for adsorbing nucleic acid can be obtained, and at the same time clogging in the pores are not easily occurred. More preferable ratio of the maximum pore size and the minimum pore size is 5 or more.

The nucleic acid-adsorbing porous membrane capable of passing though a solution internally has the percentage of porosity of preferably from 50 to 95%. More preferable percentage of porosity is from 65 to 80%. Further, it has the bubble point of preferably from 0.1 to 10 kgf/cm$^2$. More preferable bubble point is from 0.2 to 4 kgf/cm$^2$.

The nucleic acid-adsorbing porous membrane capable of passing though a solution internally has a pressure loss of preferably from 0.1 to 100 kPa. As a result, a uniform pressure can be obtained at pressurized states. More preferable pressure loss is from 0.5 to 50 kPa. Herein, the term "pressure loss" represents the minimum pressure necessary for passing water through per 100 μm thickness of a membrane.

The nucleic acid-adsorbing porous membrane capable of passing though a solution internally has an amount of water percolation, at the time of passing water through under 1 kg/cm$^2$ pressure at 25° C., of preferably 1 to 5000 mL per 1 cm$^2$ membrane for 1 minute. More preferable amount of water percolation, at the time of passing water through under 1 kg/cm$^2$ pressure at 25° C., is from 5 to 1000 mL per 1 cm$^2$ membrane for 1 minute.

The nucleic acid-adsorbing porous membrane capable of passing though a solution internally has the amount of nucleic acid-adsorption of preferably 0.1 μg or more per 1 mg of a porous membrane. More preferable amount of nucleic acid-adsorption is 0.9 μg or more per 1 mg of a porous membrane.

The nucleic acid-adsorbing porous membrane capable of passing though a solution internally has a cellulose derivative, which does not dissolve in less than 1 hour, but dissolves in less than 48 hours when a square porous membrane having a side length of 5 mm is deposited in 5 mL of trifluoroacetic acid, is preferred. A cellulose derivative, which dissolves in less than 1 hour when a square porous membrane having a side length of 5 mm is deposited in 5 mL of trifluoroacetic acid, but does not dissolve in 24 hours or less when deposited in 5 mL of dichloromethane, is also preferred. Among these, a cellulose derivative, which dissolves in less than 1 hour when a square porous membrane having a side length of 5 mm is deposited in 5 mL of trifluoroacetic acid, but does not dissolve in less than 24 hours when deposited in 5 mL of dichloromethane is more preferred.

When passing a nucleic acid mixture solution through a nucleic acid-adsorbing porous membrane, it is preferred to pass the nucleic acid mixture solution from one side to another side such that the solution is uniformly contact with the porous membrane. When passing a nucleic acid mixture solution through a nucleic acid-adsorbing porous membrane, it is preferred to pass the nucleic acid mixture solution through the nucleic acid-adsorbing porous membrane from a bigger pore size to a smaller pore size such that clogging in the pore is not occurred easily.

The flow rate, when passing a nucleic acid mixture solution through a nucleic acid-adsorbing porous membrane, is preferably from 2 to 1500 μL/sec per unit area cm$^2$ of the membrane to obtain suitable contact time of the solution to the porous membrane. When the contact time of the solution to the porous membrane is too short, sufficient separation and purification effect cannot be obtained, and when too long, it is not preferred due to its operability. The flow rate of from 5 to 700 μL/sec per unit area cm$^2$ of the membrane is more preferred.

In addition, the nucleic acid-adsorbing porous membrane capable of passing though a solution internally can be used in one layer, but also can be used in multi-layers. The multi-layers of the nucleic acid-adsorbing porous membrane may be identical to or different from each other.

The multi-layers of the nucleic acid-adsorbing porous membrane may have a combination of inorganic material and organic material of the nucleic acid-adsorbing porous membrane. For example, a combination of a glass filter and regenerated cellulose of a porous membrane can be mentioned. Further, the multi-layers of the nucleic acid-adsorbing porous membrane may have a combination of inorganic material and organic material of the nucleic acid-adsorbing porous membrane. For example, a combination of a glass filter, and nylon or polysulfone, can be mentioned.

A cartridge for separation and purification of nucleic acid comprising a container having at least two openings wherein the cartridge for separation and purification of nucleic acid receives the nucleic acid-adsorbing porous membrane, which solutions as mentioned above can pass through, in an inside of the container, can be used preferably. Further, a cartridge for separation and purification of nucleic acid comprising a container having at least two openings wherein the cartridge for separation and purification of nucleic acid receives the multi-layered nucleic acid-adsorbing porous membrane, which solutions as mentioned above can pass through, in an inside of the container, can be used preferably. In this case, the container which has at least two openings and receives the multi-layered nucleic acid-adsorbing porous membrane can be identical to or different from each other.

The cartridge for separation and purification of nucleic acid should not comprise other members except for comprising a container having at least two openings wherein the cartridge for separation and purification of nucleic acid receives the nucleic acid-adsorbing porous membrane, which solutions can pass through as mentioned above, in an inside of the container. Examples of materials for the container include plastics such as polypropylene, polystyrene, polycarbonate and polyvinyl chloride can be used. In addition, a biodegradable material can also be used preferably. Further, the container can be transparent or colored.

The cartridge for separation and purification of nucleic acid comprising the means units for distinguishing between each cartridge for separation and purification of nucleic acid can be used. The means units for distinguishing between each cartridge for separation and purification of nucleic acid may include a bar code, a 2-dimensional bar code, a magnetic tape, an IC card and the like.

In addition, the cartridge for separation and purification of nucleic acid comprising a structure in which the nucleic acid-adsorbing porous membrane can be easily taken out from a container having at least two openings can be used.

(2) Step of Passing a Washing Solution Through the Nucleic Acid-Adsorbing Porous Membrane to Wash the Porous Membrane while Adsorbing the Nucleic Acid (Washing Step)

(2) The step of passing a washing solution through a nucleic acid-adsorbing porous membrane, and washing the porous membrane while RNA is adsorbed thereto will be described below.

By the washing step, the yield and purity of finally obtained RNA is improved, and the amount of a test sample containing the necessary RNA can be minimized. Further, by automating washing and recovering operations, the operations can be simply and rapidly carried out. For the acceleration, the washing step may be completed by washing once, and if its purity is more important, several times of washing are preferred.

In the washing step, a washing solution is provided into a cartridge for separation and purification of nucleic acid receiving the nucleic acid-adsorbing porous membrane by using a tube, a pipette, an automatic injection apparatus, or a providing meansunit having the like function. The washing solution is provided from one opening of the cartridge for separation and purification of nucleic acid (the one opening where a nucleic acid mixture solution containing nucleic acid is injected). Using a pressure difference-generating apparatus connected to the one opening (e.g., a dropper, a syringe, a pump, a power pipette, etc.), the internal cartridge for separation and purification of nucleic acid was made into a pressurized state such that the washing solution is passed through the nucleic acid-adsorbing porous membrane and discharged from another different from the one opening. Also, the washing solution can be provided into one opening and discharged from the same opening. Further, the washing solution can be provided to another opening different from the one opening where the nucleic acid mixture solution containing nucleic acid is provided to, and discharged from the same opening. Among these, providing into one opening of the cartridge for separation and purification of nucleic acid, passing through nucleic acid-adsorbing porous membrane and discharging from another opening different from the one opening is more preferred due to its excellent washing efficiency.

In the washing step, the amount of a washing solution is preferably 2 $\mu$l/mm$^2$ or more. When large quantity of the washing solution is used, the washing effect could improve, but in order to maintain the operationability and prohibit the sample from discharging, 200 $\mu$l/mm$^2$ or less is preferred.

In the washing step, the flow rate, when passing a washing solution through a nucleic acid-adsorbing porous membrane, is preferably from 2 to 1500 $\mu$L/sec per unit area (cm$^2$) of the membrane, and more preferably from 5 to 700 $\mu$L/sec. In general, the passing speed is reduced to elongate the time so that washing is sufficiently carried out. However, preferably, by using the aforementioned range in the invention, the step for separating and purifying RNA can be carried out rapidly without reducing the washing efficiency.

In the washing step, the temperature of the washing solution is preferably from 4 to 70° C. Further, the temperature of the washing solution is more preferable at room temperature. In addition to the washing step, stirring using an ultrasonic or a mechanical vibration can be applied to the cartridge for separation and purification of nucleic acid at the same time. On the other hand, washing can be done by carrying out the centrifugation.

In the washing step, the washing solution is preferably a solution containing at least one of water-soluble organic solutions and water-soluble salts. It is necessary for the washing solution to have functions that works to wash out impurities in the nucleic acid mixture solution, which are adsorbed onto the nucleic acid-adsorbing porous membrane along with nucleic acid. In this regard, the washing solution must have such a composition that it desorbs only the impurities from the nucleic acid-adsorbing porous membrane, and not the nucleic acid. In the purpose, nucleic acids are very insoluble to water-soluble organic solvents such as alcohol, therefore the water-soluble organic solvents are suitable for desorbing other substances while maintaining the nucleic acid. In addition, adding water-soluble salts enables to increase an adsorption effect of nucleic acid, thereby improving the selectively removing operation for impurities and unnecessary substances.

As the water-soluble organic solvent, which is contained in a washing solution, alcohols can be used. Examples of alcohols include methanol, ethanol, isopropanol, n-isopropanol, and butanol. Any one of isopropanol and n-propanol is suitable for propanol, and any one of straight chained or branched is suitable for butanol. These alcohols can be used in multiple kinds. Among these, ethanol is preferably used.

The amount of the water-soluble organic solvent in the washing solution is preferably from 1 to 100% by weightmass, and more preferably from 5 to 40% by weightmass. In this range, DNA contamination did not increase and RNA of interest did not desorb from the porous membrane, therefore high purity and high yield of RNA was obtainable, which is preferable.

Meanwhile, the water-soluble salt contained in the washing solution is preferably a salt of halides, and among these, chloride is preferred. Further, the water-soluble salt having a monovalent or divalent cation is preferred, and alkaline metal and alkaline earth metal is particularly preferred. Among these, sodium salt, potassium salt and lithium salt is preferred, and sodium salt is most preferred.

When water-soluble salt is included in a washing solution, the concentration thereof is preferably 10 mmol/L or more. There is no problem as long as its maximum amount is in the range where it does not affect solubility of the impurities, but the concentration is preferably 1 mol/L or less and more preferably 0.1 mol/L or less. Above all, when the water-soluble salt is sodium chloride, the concentration of sodium chloride of 20 mmol/L or more is particularly preferred.

By adjusting the water-soluble salt in such a concentration, genome DNA is effectively washed, contamination of genome DNA to the recovered sample is reduced, and RNA can be separated and purified with good efficiency and high purity, while maintaining RNA on the membrane even without using DNase.

It is preferable that the washing solution does not contain a chaotropic substance. As a result, a possibility of having the chaotropic substance mixed into a recovering step (3) can be decreased. In the case where the chaotropic substance is mixed thereto in the recovering step, it sometimes hinders enzyme reaction of a RT-PCR reaction or the like, therefore considering the afterward enzyme reaction, not including the chaotropic substance in a washing solution is ideal. Further, the chaotropic substance is corrosive and harmful, in view of this, it is extremely advantageous for the researcher not to be required to use chaotropic substance in terms of security.

Herein, the chaotropic substance represents aforementioned urea, guanidine chloride, guanidine isothiocyanate, guanidine thiocyanate, sodium isothiocyanate, sodium iodide, potassium iodide or the like.

Conventionally, the washing solution has high wettability for a cartridge or the like container, thus the washing solution sometimes remains in the container during the washing step in the nucleic acid separation purification process, such that the recovering step after the washing step is contaminated with the washing solution to cause reduction of the purity of nucleic acid and reduction of the reactivity in the subsequent step. Therefore, when adsorption and desorption of nucleic acid are carried out using a cartridge or the like container, it is important that a solution, i.e., the washing solution, to be used in the adsorption or washing does not remain in the cartridge so that it does not exert influence upon the next step.

Accordingly, in order to prevent contamination of the recovering solution of the recovering step with the washing solution in the washing step, and thereby to keep residue of the washing solution in the cartridge to the minimum, it is preferable that the surface tension of the washing solution is less than 0.035 J/m². When the surface tension is low, wettability of the washing solution for the cartridge is improved, and volume of the residual solution can be controlled.

However, the proportion of water can be increased in order to increase the washing efficiency, but in that case, the surface tension of the washing solution is increased and the amount of the residual solution is increased. When the surface tension of the washing solution is 0.035 J/m² or more, the amount of the residual solution can be controlled by increasing the water repellency of the cartridge. By increasing the water repellency of the cartridge, droplets are formed, and the amount of the residual solution can be controlled by flow down of the droplets. Examples of the method for increasing water repellency include coating of a water repellant such as silicon on the cartridge surface, kneading of a water repellant such as silicon at the time of the forming a cartridge and the like, but not limited thereto.

The washing step can be simplified by making use of the nucleic acid adsorbing porous membrane of the invention. (a) Frequency of the washing solution passing through the nucleic acid adsorbing porous membrane may be reduced to once. (b) The washing step can be carried out at room temperature. (c) The subsequent step can be carried out immediately after the washing step. (d) It is also possible to combine one or two or more of the aforementioned (a), (b) and (c). In the related methods, a drying step was frequently required in order to quickly remove an organic solvent contained in the washing solution, but the nucleic acid-adsorbing porous membrane to be used in the invention is a thin membrane, thus the drying step can be omitted.

In the related RNA separation purification methods, there is a problem in that the washing solution is frequently scattered and adhered to other parts while carrying out the washing step to cause contamination (pollution) of samples. Such a type of contamination in the washing step can be inhibited by devising shapes of the cartridge for separation and purification of nucleic acid in which the nucleic acid-adsorbing porous membrane is received in a container having two openings and of the waste solution container.

It is possible to use DNase during the washing step. As a method for selectively separating and purifying RNA from a nucleic acid mixture solution containing DNA and RNA when using DNase, the method can be carried out by passing the mixture solution through a cartridge for separation and purification of nucleic acid receiving a nucleic acid-adsorbing porous membrane, where nucleic acid is adsorbed thereto (adsorbing step), followed by performing washing (washing step 1), and subjecting to DNase treatment. Moreover, the washing can be performed after subjecting to DNase treatment to remove residues such as DNase or other protein salts (washing step 2).

DNase is not particularly limited, and any DNase can be used. For example, pancreatic DNase I from an animal such as a cow, recombinant DNase prepared by the genetic recombination technology can be used.

For DNase solution (hereinafter, referred to as DNase reacting solution) in case of subjecting to DNase treatment, divalent cations such as magnesium, calcium, manganese suitable for activating DNase may be added.

Also, a buffer can be included in the DNase reacting solution to meet with the optimal pH for DNase activity. Examples of buffers used in general include TrisHCl, HEPES, phosphate buffer and the like.

In the method of the invention, the total amount of DNase solution, when designing the step of subjecting the nucleic acid-adsorbing porous membrane of the cartridge for separation and purification of nucleic acids to DNase treatment, is preferably from 5 to 550 μl per 1 cm² of the nucleic acid-adsorbing porous membrane, and more preferably 10 to 350 μl. Further, in the step of subjecting the nucleic acid-adsorbing porous membrane received in a cartridge for separation and purification of nucleic acids to DNase treatment, having the concentration of DNase in the DNase solution (hereinafter, simply referred to as the concentration of DNase) of 10 Kunitz U/mL or more and 10000 Kunitz U/mL or less is preferred, and 50 Kunitz U/mL or more and 5000 Kunitz U/mL or less is more preferred. In addition, herein used active Kunitz U is defined as "1 Kunitz U means a DNase activity that increase an absorbance of $A_{260}$ by 0.001 in 1 ml of reaction solution per one minute under the condition of using DNA as substrate at 25° C. in pH 5.0". Further, in the step of subjecting the nucleic acid-adsorbing porous membrane of a cartridge for separation and purification of nucleic acid to DNase treatment, having a time of from 5 seconds to 360 minutes is preferred, although it depends on the amount of DNA in the nucleic acid mixture solution containing DNA and RNA, and the concentration of treating DNase, and 30 seconds to 180 minutes is more preferred. Further, in the step of subjecting the nucleic acid-adsorbing porous membrane of a cartridge for separation and purification of nucleic acid to DNase treatment, having a temperature at 4° C. or more is suitable, and a temperature of from 10 to 50° C. is preferred, and having a high temperature, for example, of from 50 to 70° C. to enhance a reaction efficiency is possible. In addition, the expression "acting DNase in the nucleic acid-adsorbing porous membrane" means that DNase is reacted with the portion where nucleic acid is adsorbed to in the nucleic acid-adsorbing porous membrane, and the expression "in the nucleic acid-adsorbing porous membrane" is not limited only to the top of the nucleic acid-adsorbing porous membrane, but also in the pores of the porous membrane or the exit of the pores in the backside of the membrane or the like is comprised thereto.

In addition, to the DNase reaction solution, metal salts belonging to Group 2 of the Periodic Table of Elements, sodium salts, lithium salts, potassium salts and the like can be added for maintaining nucleic acids on the nucleic acid-adsorbing porous membrane. As a metal salt belonging to Group 2 of the Periodic Table of Elements, a magnesium salt can be used preferably, and as a magnesium salt, magnesium chloride or magnesium sulfate is more preferred. When using a magnesium salt, any one of magnesium chloride and magnesium sulfate may be used alone or both can be used. Using magnesium chloride and magnesium sulfate is preferable in that both functions to express DNase activity and maintain nucleic acids to the nucleic acid-adsorbing porous membrane are satisfied. The concentration when using magnesium chloride and magnesium sulfate is preferably from 10 to 500 mmol/L, and more preferably from 10 to 200 mmol/L.

(3) Step of Passing the Recovering Solution Through the Nucleic Acid-Adsorbing Porous Membrane to Desorb the Nucleic Acid from the Porous Membrane (Recovering Step)

(3) A step of passing the recovering solution through the nucleic acid-adsorbing porous membrane to desorb the nucleic acid from the porous membrane will be described below.

The recovering solution is provided to the cartridge for separation and purification of nucleic acid receiving the nucleic acid-adsorbing porous membrane, by using a tube, a pipette, an automatic injection apparatus or a providing meansunit having the like function. The recovering solution is provided from one opening of the cartridge for separation and purification of nucleic acid (the one opening where a nucleic acid mixture solution containing nucleic acid is injected), and a pressure difference-generating apparatus connecting to the one opening (e.g., a dropper, a syringe, a pump, a power pipette, etc.) is used, thereby making an inside of the cartridge for separation and purification of nucleic acid into a pressurized state, so as to pass the recovering solution through the nucleic acid-adsorbing porous membrane, and discharge the recovering solution from another opening different from the one opening. Additionally, the recovering solution can be provided into one opening and discharged from the same opening. Further, the recovering solution can be provided to another opening different from the one opening which the nucleic acid mixture solution containing nucleic acid is provided to, and discharged from the same opening. Among these, providing into one opening of the cartridge for separation and purification of nucleic acid, passing through nucleic acid-adsorbing porous membrane and discharging from another opening different from the one opening is more preferred due to its excellent recovering efficiency.

Considering the volume of the nucleic acid mixture solution prepared from the test sample, the desorption of RNA can be carried out by controlling the volume of the recovering solution. The amount of the recovering solution containing separated and purified RNA, that is, the amount of RNA solution discharged out from the cartridge container and recovered is related to the amount of a test sample used at the time. In general, the amount of the recovering solution commonly used is from several tens µl to several hundreds but either extremely small quantity of a test sample is used or a large amount of RNA is desired to be separated and purified, the amount of the recovering solution can be changed in a range of 1 µl to several tens ml.

As the recovering solution, purified distilled water, a Tris buffer, a Tris/EDTA buffer and the like can be used preferably. Further, when providing the recovered RNA to RT-PCR (Reverse Transcription Polymerase Chain Reaction) after the step, the buffer solution (e.g., an aqueous solution having the final concentration of 75 mmol/L of KCl, 50 mmol/L of Tris-HCl, 3.0 mmol/L of $MgCl_2$, 10 mmol/L of DDT) for RT-PCR can be used.

The pH of the recovering solution is preferably from pH 1 to 10. Considering the stability of RNA, the pH being neutral to acidic is preferred, thus pH 2 to 7 is preferred. Especially, ion strength and the salt concentration have effects on the elution of adsorbed RNA. The recovering solution having 500 mmol/L or less of ion strength is preferred. The salt concentration is preferably 0.5 mol/L or less, and more preferably 0.01 mmol/L or more and 50 mmol/L or less. Thereby, the yield of RNA is increased, and a larger amount of RNA can be recovered.

The recovering solution containing concentrated RNA can be obtained by reducing volume of the recovering solution in comparison with the volume of the original nucleic acid mixture solution. Preferably, (volume of the recovering solution): (volume of the nucleic acid mixture solution)=1:100 to 99:100, and more preferably, (volume of the recovering solution): (volume of the nucleic acid mixture solution)=1:10 to 9:10. Thereby, RNA can be conveniently concentrated without carrying out an operation for concentration in the after-step of the nucleic acid separation purification. By these methods, a method for obtaining RNA solution in which RNA is concentrated than the test sample can be provided.

In addition, as another aspect, a recovering solution containing a desired concentration of RNA can be obtained, and a recovering solution containing a concentration of RNA suited for the subsequent step (e.g., RT-PCR or the like) can be obtained, by carrying out desorption of RNA under such a condition that volume of the recovering solution becomes larger than the volume of the original nucleic acid mixture solution. Preferably, (volume of the recovering solution): (volume of the nucleic acid mixture solution)=1:1 to 50:1, and more preferably, (volume of the recovering solution):

(volume of the nucleic acid mixture solution)=1:1 to 5:1. Thereby, a merit, namely avoidance of the troublesome concentration adjustment after the separation and purification of nucleic acid, can be obtained. In addition, increase of RNA yield from the porous membrane can be made by the use of sufficient amount of the recovering solution.

Also, RNA can be conveniently recovered by changing the temperature of the recovering solution in response to the purpose. For example, RNA solution can be obtained conveniently and efficiently, by preventing degradation of RNA through the inhibition of the action of ribonuclease without adding a certain reagent or a specific operation capable of inhibiting enzymatic degradation, by carrying out desorption of RNA from the porous membrane after changing the temperature of the recovering solution to 0 to 10° C.

Further, when the temperature of the recovering solution is set to 10 to 35° C., recovery of RNA at typical room temperature can be carried out, and the RNA can be separated and purified by the desorption without requiring a complex step.

In addition, as another aspect, the desorption of RNA from the porous membrane can be carried out conveniently with high yield without mediating a complicated operation, by shifting temperature of the recovering solution to a high temperature of, for example, from 35 to 70° C.

The number of times of injection of the recovering solution is not limited, but it may be once or multiple times. In general, when RNA is separated and purified quickly and conveniently, the injection of the recovering solution is carried out once, but when a large amount of RNA is recovered, the recovering solution may be injected multiple times.

In the recovering step, it is possible to make the RNA solution into a composition which can be used in the after-step. The separated and purified RNA is sometimes applied to the RT-PCR (Reverse Transcription Polymerase Chain Reaction) method. In that case, the separated and purified RNA solution is required to be diluted with a buffer solution suited for the RT-PCR method. By using a buffer solution suited for the RT-PCR method in the recovery step according to this method, it can be shifted to the subsequent RT-PCR step conveniently and quickly.

Also, in the recovering step, it is possible to add a stabilizing agent for preventing degradation of RNA after discharged from the cartridge and recovered in the recovering solution. As the stabilizing agent, an antibacterial agent, a fungicide, a nucleic acid degradation inhibitor and the like can be added. As the nuclease inhibitor, a nuclease inhibitor, specifically EDTA and the like can be mentioned. In addition, as another embodiment, a stabilizer can also be added to the recovery container in advance.

The recovery container to be used in the recovering step is not particularly limited, but a recovery container prepared from a raw material having no absorption at 260 nm can be used. In that case, the concentration of the recovered RNA solution can be measured without transferring it into other container. Examples of the raw material having no absorption at 260 nm including quartz glass and the like can be used, but not limited thereto.

<Kit>

It is possible to make the cartridge, reagents and the like for carrying out the RNA separation and purification method of the invention described above into a kit. Specifically, the kit comprises (i) a cartridge for separating and purifying nucleic acid which received a nucleic acid-adsorbing porous membrane together with reagents such as (ii) a hemolytic agent, (iii) a nucleic acid-solubilizing reagent, (iv) a washing solution and (v) a recovering solution.

<Automated Apparatus>

As described above, the method for separating and purifying RNA from a test sample containing nucleic acid by using a cartridge for separation and purification of nucleic acid receiving the nucleic acid-adsorbing porous membrane in a container having at least two openings and a pressure difference-generating apparatus, can be carried out by using an automated apparatus which proceeds the steps automatically comprised in the method. In addition, the method can be carried out by using an automated apparatus which precedes the use of aforementioned kit automatically. As a result, not only the operation has simplified and accelerated, but also became possible to obtain a certain level of RNA, independent from the skills of operators.

The automated apparatus which automatically proceeds the steps of separating and purifying RNA from a test sample containing nucleic acid by using a cartridge for separation and purification of nucleic acid receiving the nucleic acid-adsorbing porous membrane in a container having at least two openings and a pressure difference-generating apparatus, is exemplified below, but the automated apparatus of the invention is not limited thereto.

An automated apparatus is an apparatus for separating and purifying RNA automatically performing the operations for separation and purification comprising the steps of: using a cartridge for separation and purification of nucleic acid receiving a nucleic acid-adsorbing porous membrane capable of passing though solutions internally; injecting a nucleic acid mixture solution containing DNA and RNA into the cartridge for separation and purification of nucleic acid, so as to adsorb nucleic acid in the nucleic acid mixture solution onto the nucleic acid-adsorbing porous membrane by pressurizing, injecting a washing solution into the cartridge for separation and purification of nucleic acid, so as to remove the impurities by pressurizing; injecting a recovering solution into the cartridge for separation and purification of nucleic acid, so as to desorb the adsorbed RNA from the nucleic acid-adsorbing porous membrane and recover the desorbed RNA along with recovering solution. The automated apparatus comprises: a loading unit which maintains the cartridge for separation and purification of nucleic acid, a waste solution container receiving the discharged solution of the sample solution and the washing solution, and a recovering container receiving the recovering solution containing recovered RNA (RNA solution); a pressurized air supplying unit which introduce a pressurized air into the cartridge for separation and purification of nucleic acid; and an injecting unit which injects the washing solution and the recovering solution into the cartridge for separation and purification of nucleic acid.

Moreover, the automated apparatus is an apparatus for selectively separating and purifying RNA automatically performing the operations for separation and purification comprising the steps of: injecting DNase into the cartridge for separation and purification of nucleic acid during the washing step, so as to the nucleic acid-adsorbing porous membrane to DNase; injecting the washing solution into the cartridge for separation and purification of nucleic acid after passing DNase through the nucleic acid-adsorbing porous membrane internally by pressurizing; injecting a recovering solution into the cartridge for separation and purification of nucleic acid, so as to remove the impurities by pressurizing; injecting a recovering solution into the cartridge for separation and purification of nucleic acid after removing degraded DNA by pressurizing, so as to desorb the adsorbed RNA from the nucleic acid-adsorbing porous membrane and recover the desorbed RNA along with recovering solution. It is preferable that the automated apparatus comprises: a loading unit which maintains the cartridge for separation and purification of nucleic acid, a waste solution container receiving the nucleic acid mixture solution residue, the discharged solution of DNase and the washing solution, and a recovering container receiving the recovering solution containing recovered RNA; a pressurized air supplying unit which introduce a pressurized air into the cartridge for separation and purification of nucleic acid; and an injecting unit which injects the washing solution, DNase and the recovering solution into the cartridge for separation and purification of nucleic acid.

The loading unit preferably comprises: a stand loaded onto the main apparatus; a cartridge holder, which maintains the cartridge for separation and purification of nucleic acid, supported by the stand capable of moving up and down; and a container holder which maintains the waste solution container and the recovering container capable of exchanging their positions against the cartridge for separation and purification of nucleic acid under the cartridge holder.

The pressurized air supplying unit preferably comprises: an air nozzle which spouts pressurized air from the bottom portion; a pressurized-head which moves the air nozzle up and down depending on the cartridge for separation and purification of nucleic acid maintained to the cartridge holder by supporting the air nozzle; and a position determining meansunit installed in the pressurized-head which determines the position of the cartridge for separation and purification of nucleic acid in the rack of the loading unit.

Further, the injecting unit preferably comprises: a washing solution injecting nozzle which injects the washing solution; a recovering solution injecting nozzle which injects the recovering solution; a nozzle transfer board which can move sequentially on the cartridge for separation and purification of nucleic acid maintained to the loading unit with maintaining the DNase injecting nozzle, if necessary; a washing solution supplying pump which supplies the washing solution to the washing solution injecting nozzle by sucking the washing solution from a washing solution bottle receiving the washing-solution; a recovering solution supplying pump which supplies the recovering solution to the recovering solution injecting nozzle by sucking the recovering solution from a recovering solution bottle receiving the recovering solution; and, if necessary, a DNase supplying pump which supplies DNase to the DNase injecting nozzle by sucking DNase from a DNase bottle receiving DNase.

According to an automated apparatus, for example aforementioned automated apparatus comprising: the cartridge for separation and purification of nucleic acid; the loading unit which maintains the waste solution container and the recovering container; the pressurized air supplying unit which introduces a pressurized air into the cartridge for separation and purification of nucleic acid; and the injecting unit which injects a washing solution, a recovering solution and, if necessary, DNase into the cartridge for separation and purification of nucleic acid, the separation and purification of RNA is carried out automatically comprising the steps of: injecting a sample solution containing nucleic acid into the cartridge for separation and purification of nucleic acid receiving the nucleic acid-adsorbing porous membrane, so as to adsorb nucleic acid onto the nucleic acid-adsorbing porous membrane by pressurizing; injecting a washing solution, so as to wash and discharge the impurities; injecting a recovering solution, so as to desorb the adsorbed RNA from the nucleic acid-adsorbing porous membrane, and recovering the desorbed RNA, and the units which can automatically separate and purify RNA in a mixture solution in a short time with high efficiency can be compactly constituted.

Further, when the loading unit is constituted of a stand, a cartridge holder, which enables up and down movement maintaining the cartridge for separation and purification of nucleic acid; and a container holder which maintains the waste solution container and the recovering container capable of exchanging their positions, a cartridge for separation and purification of nucleic acid and both container sets, and the waste solution container and the recovering container can be easily exchanged.

Further, when the pressurized air supplying unit is constituted of an air nozzle, a pressurized-head head which moves the air nozzle up and down and a position determining meansunit which determines position of the cartridge for separation and purification of nucleic acid, a reliable supply of a pressurized air can be performed with a simple unit.

Further, when the injecting unit is constituted of a washing solution injecting nozzle, a recovering solution injecting nozzle, a nozzle transfer board which can move subsequently on the cartridge for separation and purification of nucleic acid, a washing solution supplying pump which supplies the washing solution to the washing solution injecting nozzle by sucking the washing solution from a washing solution bottle and the recovering solution supplying pump which supplies the recovering solution to the recovering solution injecting nozzle by sucking the recovering solution from a recovering solution bottle, the sequential injections of the washing solution and the recovering solution can be performed with a simple unit.

EXAMPLES

Hereinafter, the present invention will be described in detail according to Examples, but the invention is not limited the following Examples.

Example 1

(1) Preparation of Cartridge for Separation and Purification of Nucleic Acid

A cartridge for separation and purification of nucleic acid having a portion for receiving the nucleic acid-adsorbing porous membrane with an inner diameter of 7 mm and capable of holding 800 µl of a solution was prepared.

(2) For the nucleic acid-adsorbing porous membrane, a porous membrane which is the saponified porous membrane of triacetyl cellulose was used, and the nucleic acid-adsorbing porous membrane was received in the portion for receiving the nucleic acid-adsorbing porous membrane of the cartridge for separation and purification of nucleic acid prepared in the above (1).

(3) Preparation of Hemolytic Agent, Nucleic Acid-Solubilizing Reagent, Washing Solution and Recovering Solution A hemolytic agent A, a nucleic acid-solubilizing reagent A1 and A2, a washing solution A and a recovering solution A were prepared according to the formulation indicated below.

| (Hemolytic agent A) | |
|---|---|
| Ammonium chloride | 150 mmol/L |
| Sodium hydrogen carbonate | 10 mmol/L |
| EDTA (pH 8.0) | 0.1 mmol/L |

-continued (Nucleic acid-solubilizing reagent A1)

| | |
|---|---|
| Guanidine thiocyanate (manufactured by Wako Pure Chemical Industries, Ltd.) | 3.5 mmol/L |
| BisTris (manufactured by Dojindo Laboratories) pH was adjusted to 6.5 using hydrochloric acid 1.0 vol % of 2-mercaptoethanol was added just before the use of nucleic acid-solubilizing reagent A1. | 0.25 mmol/L |

(Nucleic acid-solubilizing reagent A2)

| | |
|---|---|
| Tween 20 (manufactured by Wako Pure Chemical Industries, Ltd.) | 15 mass % |
| BisTris (manufactured by Dojindo Laboratories) pH was adjusted to 6.0 using hydrochloric acid | 0.1 mmol/L |

(Washing solution A)

| | |
|---|---|
| Tris-HCl (pH 7.5) | 10 mmol/L |
| Sodium chloride | 100 mmol/L |
| Ethanol | 30 vol % |

(Recovering solution A)

| | |
|---|---|
| Tris-HCl (pH 6.5) | 1 mmol/L |

(4) Preparation of Nucleic Acid Mixture Solution

Human whole blood, which was treated with EDTA-2Na as an anticoagulant, (total number of the white blood cells of $3\times10^{56}$, $1\times10^7$, $1.5\times10^7$, $3\times10^7$ and $4\times10^7$) were transferred to 50 mL-conical tubes, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 400×g for 10 minutes at 4° C., and then the supernatant solution was completely removed. After removing the supernatant solution, the hemolytic agent A in the amount of twice the amount of the original whole blood was added into the containers. Light Vortex mixing was carried out for 5 seconds to suspend the cells, centrifuged at 400×g for 10 minutes at 4° C., and then the supernatant solution was completely removed. To the leukocyte pellets obtained in the above, 350 μl of the nucleic acid-solubilizing reagent A1 was added, and the samples were transferred to 1.5 mL microtubes. Leukocyte was dissolved by means of Vortex mixing for 1 minute. Here, 175 μl of the nucleic acid-solubilizing reagent A2 was added and stirred using a Vortex mixer for 15 seconds. 175 μl of 99.5 vol % or more superhigh-grade ethanol was further added and stirred using a Vortex mixer for 1 minute.

(5) Operation for Separating and Purifying RNA

The mixture solution of nucleic acid obtained from the above was injected into one opening of the cartridge for separation and purification of nucleic acid having the nucleic acid-adsorbing porous membrane prepared in (1) and (2) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected mixture sample solution containing nucleic acid through the nucleic acid-adsorbing porous membrane and discharged from another opening of the cartridge for separation and purification of nucleic acid. Subsequently, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. The same operation was repeated three times. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The time needed to operate separation and purification of RNA was less than 5 minutes per one sample for all the samples with different number of white blood cells.

(6) Yield and Purity of Recovered Nucleic Acid

The yield and purity (260/280) of RNA recovered in Example 1 are presented in Table 1.

TABLE 1

| Number of white blood cells | Yield of RNA [μg] | 260/280 |
|---|---|---|
| $3 \times 10^6$ | 1.8 | 2.0 |
| $1 \times 10^7$ | 2.3 | 2.0 |
| $1.5 \times 10^7$ | 3.8 | 2.0 |
| $3 \times 10^7$ | 5.6 | 2.0 |
| $4 \times 10^7$ | 8.4 | 2.0 |

Therefore, it was possible to recover high purity RNA conveniently from leukocyte.

Example 2

(7) Preparation of Cartridge for Separation and Purification of Nucleic Acid

A cartridge for separation and purification of nucleic acid having a portion for receiving the nucleic acid-adsorbing porous membrane with an inner diameter of 7 mm and capable of holding 7 ml of a solution was prepared.

(8) For the nucleic acid-adsorbing porous membrane, a porous membrane which is the saponified porous membrane of triacetyl cellulose was used, and the nucleic acid-adsorbing porous membrane was received in the portion for receiving the nucleic acid-adsorbing porous membrane of the cartridge for separation and purification of nucleic acid prepared in the above (7).

(9) Preparation of Hemolytic Agent, Nucleic Acid-Solubilizing Reagent, Washing Solution and Recovering Solution In the same manner as in Example 1, a hemolytic agent A, a nucleic acid-solubilizing reagent A1 and A2, a washing solution A and a recovering solution A were prepared.

(10) Preparation of Nucleic Acid Mixture Solution

Human whole blood, which was treated with EDTA-2Na as an anticoagulant, (total number of the white blood cells of $1.5 \times 10^7$, $3 \times 10^7$, $6 \times 10^7$ and $8 \times 10^7$) were transferred to 50 mL-conical tubes, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 400×g for 10 minutes at 4° C., and then the supernatant solution was completely removed. After removing the supernatant solution, the hemolytic agent A in the amount of twice the amount of the original whole blood was added into the containers. Light Vortex mixing was carried out for 5 seconds to suspend the cells, centrifuged at 400×g for 10 minutes at 4° C., and then the supernatant solution was completely removed. To the leukocyte pellets obtained in the above, 2 ml of the nucleic acid-solubilizing reagent A1 was added, and leukocyte was dissolved by means of Vortex mixing for 1 minute. Here, 1 ml of the nucleic acid-solubilizing reagent A2 was added and stirred using a Vortex mixer for 15 seconds. 1 ml of 99.5 vol % or more superhigh-grade ethanol was further added and stirred using a Vortex mixer for 1 minute.

(11) Operation for Separating and Purifying RNA

The mixture solution of nucleic acid obtained from the above was injected into one opening of the cartridge for separation and purification of nucleic acid having the nucleic acid-adsorbing porous membrane prepared in (7) and (8) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 4.5 ml of the washing solution A was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. The same operation was repeated three times. Next, 500 µl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The time needed to operate separation and purification of RNA was less than 8 minutes per one sample for all the samples with different number of white blood cells.

(12) Yield and Purity of Recovered Nucleic Acid

The yield and purity (260/280) of RNA recovered in Example 2 are presented in Table 2.

TABLE 2

| Number of white blood cells | Yield of RNA [µg] | 260/280 |
| --- | --- | --- |
| $1.5 \times 10^7$ | 7.2 | 2.0 |
| $3 \times 10^7$ | 14.6 | 2.0 |
| $6 \times 10^7$ | 22.6 | 2.0 |
| $8 \times 10^7$ | 38.4 | 2.0 |

Therefore, it was possible to recover high purity RNA conveniently from leukocyte.

Example 3

(13) Preparation of Cartridge for Separation and Purification of Nucleic Acid

A cartridge for separation and purification of nucleic acid having a portion for receiving the nucleic acid-adsorbing porous membrane with an inner diameter of 20 mm and capable of holding 10 ml of a solution was prepared.

(14) For the nucleic acid-adsorbing porous membrane, a porous membrane which is the saponified porous membrane of triacetyl cellulose was used, and the nucleic acid-adsorbing porous membrane was received in the portion for receiving the nucleic acid-adsorbing porous membrane of the cartridge for separation and purification of nucleic acid prepared in the above (13).

(15) Preparation of Hemolytic Agent, Nucleic Acid-Solubilizing Reagent, Washing Solution and Recovering Solution In the same manner as in Example 1, a hemolytic agent A, a nucleic acid-solubilizing reagent A1 and A2, a washing solution A and a recovering solution A were prepared.

(16) Preparation of Nucleic Acid Mixture Solution

Human whole blood, which was treated with EDTA-2Na as an anticoagulant, (total number of the white blood cells of $1 \times 10^7$, $3 \times 10^7$ and $6 \times 10^7$) were transferred to 50 mL-conical tubes, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 400×g for 10 minutes at 4° C., and then the supernatant solution was completely removed. After removing the supernatant solution, the hemolytic agent A in the amount of twice the amount of the original whole blood was added into the containers. Light Vortex mixing was carried out for 5 seconds to suspend the cells, centrifuged at 400×g for 10 minutes at 4° C., and then the supernatant solution was completely removed. To the leukocyte pellets obtained in the above, 2 ml of the nucleic acid-solubilizing reagent A1 was added, and leukocyte was dissolved by means of Vortex mixing for 1 minute. Here, 1 ml of the nucleic acid-solubilizing reagent A2 was added and stirred using a Vortex mixer for 15 seconds. 1 ml of 99.5 vol % or more superhigh-grade ethanol was further added and stirred using a Vortex mixer for 1 minute.

(17) Operation for Separating and Purifying RNA

The mixture solution of nucleic acid obtained from the above was injected into one opening of the cartridge for separation and purification of nucleic acid having the nucleic acid-adsorbing porous membrane prepared in (13) and (14) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 4.5 ml of the washing solution A was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. The same operation was repeated three times. Next, 500 µl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The time needed to operate separation and purification of RNA was less than 1 minute and half per one sample for all the samples with different number of white blood cells.

(18) Yield and Purity of Recovered Nucleic Acid

The yield and purity (260/280) of RNA recovered in Example 3 are presented in Table 3.

TABLE 3

| Number of white blood cells | Yield of RNA [µg] | 260/280 |
|---|---|---|
| $1 \times 10^7$ | 4.6 | 2.0 |
| $3 \times 10^7$ | 10.7 | 2.0 |
| $6 \times 10^7$ | 17.7 | 2.0 |

Therefore, it was possible to recover high purity RNA conveniently from leukocyte.

Example 4

(19) Preparation of Cartridge for Separation and Purification of Nucleic Acid

A cartridge for separation and purification of nucleic acid having a portion for receiving the nucleic acid-adsorbing porous membrane with an inner diameter of 7 mm and capable of holding 800 µl of a solution was prepared.

(20) For the nucleic acid-adsorbing porous membrane, a porous membrane which is the saponified porous membrane of triacetyl cellulose was used, and the nucleic acid-adsorbing porous membrane was received in the portion for receiving the nucleic acid-adsorbing porous membrane of the cartridge for separation and purification of nucleic acid prepared in the above (19).

(21) Preparation of Hemolytic Agent, Nucleic Acid-Solubilizing Reagent, Washing Solution and Recovering Solution The solutions accompanying the QIAamp RNA Blood Mini Kit manufactured by QIAGEN Inc. were used.

(Hemolytic agent) Buffer EL: containing ammonium chloride (Nucleic acid-solubilizing reagent) RTL: containing guanidine thiocyanate (Washing solution-1) RW1

(Washing solution-2) RPE (containing 80 vol % of EtOH)

(Recovering solution) RNase-free water

(22) Preparation of Nucleic Acid Mixture Solution

Human whole blood, which was treated with EDTA-2Na as an anticoagulant, (total number of the white blood cells of $1 \times 10^7$) was transferred to 50 mL-conical tube, and the Buffer EL in the amount of 5 times the amount of whole blood was added thereto and incubated on ice for 15 minutes. During the incubation, Vortex mixing was carried out twice. The blood suspension becoming transparent was confirmed, centrifuged at 400×g for 10 minutes at 4° C., and then the supernatant solution was completely removed. After removing the supernatant solution, the hemolytic agent A in the amount of twice the amount of the original whole blood was added into the container. Light Vortex mixing was carried out for 5 seconds to suspend the cells, centrifuged at 400×g for 10 minutes at 4° C., and then the supernatant solution was completely removed. The leukocyte pellet obtained in the above was transferred to 1.5 mL microtube, and 350 µl of RLT was added. Leukocyte was dissolved by means of Vortex mixing for 1 minute. Here, 350 µl of 70 vol % or more superhigh-grade ethanol was added and stirred using a Vortex mixer for 1 minute.

(23) Operation for Separating and Purifying RNA

The mixture solution of nucleic acid obtained from the above was injected into one opening of the cartridge for separation and purification of nucleic acid having the nucleic acid-adsorbing porous membrane prepared in (19) and (20) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 µl of the washing solution-1 was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. Subsequently, 500 µA of the washing solution-2 was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. The same operation was repeated twice. Next, 50 μl of the recovering solution was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The time needed to operate separation and purification of RNA was less than 1 minute. The operation time even was shorter than Example 1.

(24) Yield and Purity of Recovered Nucleic Acid

The yield and purity (260/280) of RNA recovered in Example 4 are presented in Table 4.

TABLE 4

| Number of white blood cells | Yield of RNA [μg] | 260/280 |
|---|---|---|
| $1 \times 10^7$ | 2.8 | 1.9 |

Therefore, it was possible to recover high purity RNA conveniently from leukocyte, although the solution accompanying the QIAamp RNA Blood Mini Kit manufactured by QIAGEN Inc. were used.

Example 5

(25) Preparation of Cartridge, Hemolytic Agent, Nucleic Acid-Solubilizing Reagent, Washing Solution and Recovering Solution In the same manner as in Example 1, a cartridge, a hemolytic agent A, a nucleic acid-solubilizing reagent A1 and A2, a washing solution A and a recovering solution A were prepared.

(26) Preparation of Nucleic Acid Mixture Solution

Human whole blood, which was treated with EDTA-2Na as an anticoagulant, (total number of the white blood cells of $5 \times 10^6$ and $1 \times 10^7$) were transferred to 50 mL-conical tubes, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 400×g for 10 minutes at 4° C., and then the supernatant solution was completely removed. After removing the supernatant solution, the hemolytic agent A in the amount of twice the amount of the original whole blood was added into the containers. Light Vortex mixing was carried out for 5 seconds to suspend the cells, centrifuged at 400×g for 10 minutes at 4° C., and then the supernatant solution was completely removed. To the leukocyte pellets obtained in the above, 350 μl of the nucleic acid-solubilizing reagent A1 was added, and leukocyte was dissolved by means of Vortex mixing for 1 minute. Here, 175 μl of the nucleic acid-solubilizing reagent A2 was added and stirred using a Vortex mixer for 15 seconds. 175 μl of 99.5 vol % or more superhigh-grade ethanol was further added and stirred using a Vortex mixer for 1 minute.

(27) Operation for Separating and Purifying RNA

The mixture solution of nucleic acid obtained from the above was injected into one opening of the cartridge for separation and purification of nucleic acid having the nucleic acid-adsorbing porous membrane prepared in (25) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. After taking off the pressure difference-generating apparatus, 40 μl (104 μl/cm$^2$) of DNase solution (RQ1 RNase-Free DNase 500 Kunitz U/L, manufactured by Promega Corp. was used) was applied onto the membrane, and was left to stand for 5 minutes at room temperature. The same operation of washing as in the above was repeated twice. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The time needed to operate separation and purification of RNA was less than 6 minutes, which includes DNase reaction time, per 1 sample in each number of white blood cells.

(28) Yield and Purity of Recovered Nucleic Acid

The yield and purity (260/280) of RNA recovered in Example 5 are presented in Table 5.

TABLE 5

| Number of white blood cells | Yield of RNA [μg] | 260/280 |
|---|---|---|
| $5 \times 10^6$ | 1.0 | 2.0 |
| $1 \times 10^7$ | 2.0 | 2.0 |

(29) Electrophoresis of Recovered Nucleic Acid

The electrophoretic profile of RNA recovered in Example 5 is shown in FIG. 1. High purity RNA can be obtained by completely removing DNA by subjecting to the DNase treatment.

Example 6

(30) Preparation of Cartridge, Hemolytic Agent, Nucleic Acid-Solubilizing Reagent, Washing Solution and Recovering Solution In the same manner as in Example 1, a cartridge, a hemolytic agent A, a nucleic acid-solubilizing reagent A1, a washing solution A and a recovering solution A were prepared.

(31) Preparation of Nucleic Acid Mixture Solution

Human whole blood, which was treated with EDTA-2Na as an anticoagulant, (total number of the white blood cells of $1.5 \times 10^7$) was transferred to 50 mL-conical tube, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 400×g for 10 minutes at 4° C., and then the supernatant solution was completely removed. After removing the supernatant solution, the hemolytic agent A in the amount of twice the amount of the original whole blood was added into the container. Light Vortex mixing was carried out for 5 seconds to suspend the cells, centrifuged at 400×g for 10 minutes at 4° C., and then the supernatant solution was completely removed. To the leukocyte pellet obtained in the above, 520 μl of the nucleic acid-solubilizing reagent A1 was added, and the pellet was loosened by pipetting. Leukocyte was dissolved by means of Vortex mixing for 1 minute. Here, 173 μl of 99.5 vol % or more superhigh-grade ethanol was added i.e., the concentration of ethanol became 25 vol %, and stirred using a Vortex mixer for 1 minute. In addition, the sample solutions were prepared in the same manner except that 223, 250 and 280 μl of 99.5 vol % or more superhigh-grade ethanol were added respectively instead of adding 173 μl of 99.5 vol % or more superhigh-grade ethanol. That is, the concentration of ethanol became 25, 30, 32.5 and 35 vol %, respectively, and then the solutions were stirred using a Vortex mixer for 1 minute.

(32) Operation for Separating and Purifying RNA

The mixture solution of nucleic acid obtained from the above was injected into one opening of the cartridge for separation and purification of nucleic acid having the nucleic acid-adsorbing porous membrane prepared in (30) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. The same operation was repeated three times. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The recovery was repeated twice. The time needed to operate separation and purification of RNA was less than 2 minutes per 1 sample in each number of white blood cells.

(33) Yield and Purity of Recovered Nucleic Acid

The yield and purity (260/280) of RNA are presented in Table 6.

TABLE 6

| Concentration of ethanol (vol %) | Yield of RNA [μg] (recovery 1) | Yield of RNA [μg] (recovery 2) | 260/280 |
|---|---|---|---|
| 25 | 1.7 | 1.8 | 2.0 |
| 30 | 5.5 | 1.4 | 2.0 |
| 32.5 | 6.2 | 1.1 | 2.1 |
| 35 | 5.4 | 1.1 | 2.1 |

Therefore, it was possible to recover high purity RNA conveniently from leukocyte with any concentration of ethanol.

Example 7

(34) Preparation of Cartridge for Separation and Purification of Nucleic Acid A cartridge for separation and purification of nucleic acid having a portion for receiving the nucleic acid-adsorbing porous membrane with an inner diameter of 7 mm and capable of holding 800 μl of a solution was prepared.

(35) For the nucleic acid-adsorbing porous membrane, a porous membrane which is the saponified porous membrane of triacetyl cellulose was used, and three sheets of the nucleic acid-adsorbing porous membrane one on top of another were received in the portion for receiving the nucleic acid-adsorbing porous membrane of the cartridge for separation and purification of nucleic acid prepared in the above (34).

(36) Preparation of Hemolytic Agent, Nucleic Acid-Solubilizing Reagent A1, Washing Solution and Recovering Solution In the same manner as in Example 1, a cartridge, a hemolytic agent A, a nucleic acid-solubilizing reagent A1, a washing solution A and a recovering solution A were prepared.

(37) Preparation of Nucleic Acid Mixture Solution

Human whole blood, which was treated with EDTA-2Na as an anticoagulant, (total number of the white blood cells of $1 \times 10^7$) was transferred to 50 mL-conical tube, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 2000×g for 2 minutes at 4° C., and then the supernatant solution was completely removed. After removing the supernatant solution, the hemolytic agent A in the amount of twice the amount of the original whole blood was added into the container. Light Vortex mixing was carried out for 5 seconds to suspend the cells, centrifuged at 2000×g for 2 minutes at 4° C., and then the supernatant solution was completely removed. To the leukocyte pellet obtained in the above, 520 μl of the nucleic acid-solubilizing reagent A1 was added, and the pellet was loosened by pipetting. Leukocyte was dissolved by means of Vortex mixing for 30 seconds. Here, 250 μl of 99.5 vol % or more superhigh-grade ethanol was added i.e., the concentration of ethanol became 32.5 vol %, and stirred using a Vortex mixer for 5 minute.

(38) Operation for Separating and Purifying RNA

The mixture solution of nucleic acid obtained from the above was injected into one opening of the cartridge for separation and purification of nucleic acid having the nucleic acid-adsorbing porous membrane prepared in (34) and (35) above, subsequently, a pressure difference-generating apparatus was connected to the one opening to make an inside of the cartridge for separation and purification of nucleic acid into a pressurized state (160 kPa). The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state (160 kPa). The injected washing solution was passed through the nucleic acid-adsorbing porous membrane and discharged from another opening. After taking off the pressure difference-generating apparatus, 120 μl (312 μl/cm$^2$) of DNase solution (DNase I, Amplification Grade 500 Kunitz U/L, manufactured by Sigma Corp. was used) was applied onto the membrane, and was left to stand for 15 minutes at room temperature. The same operation of washing as in the above was repeated twice. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state (160 kPa). The injected recovering solution was passed through the nucleic acid-adsorbing porous membrane, discharged from another opening, thereby the eluted solution was recovered. The time needed to operate separation and purification of RNA was less than 16.5 minutes, which includes DNase reaction time, per 1 sample in each number of white blood cells.

(39) Yield and Purity of Recovered Nucleic Acid

The yield and purity (260/280) of RNA recovered in Example 7 are presented in Table 7.

TABLE 7

| Number of white blood cells | Yield of RNA [μg] | 260/280 |
|---|---|---|
| 1 × 10$^7$ | 4.7 | 2.2 |
| 1 × 10$^7$ | 5.0 | 2.2 |

(40) Electrophoresis of Recovered Nucleic Acid

Figure 2:
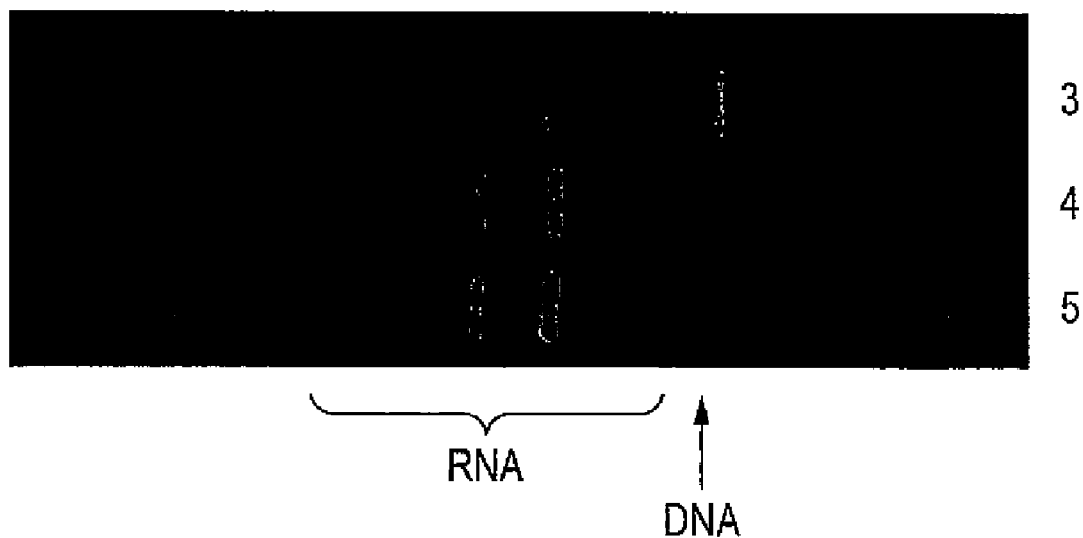
FIG. 2 is a diagram of a photograph obtained by subjecting RNA, which was obtained from human whole blood containing total white blood cell number of $1 \times 10^7$ and was separated and purified according to the method of the invention, to agarose gel (TAE migration buffer) electrophoresis, wherein 1: denotes RNA obtained from human whole blood having total white blood cell number of $5 \times 10^6$.

The electrophoretic profile of RNA recovered in Example 7 is shown in FIG. 2. High purity RNA can be obtained by completely removing DNA by subjecting to the DNase treatment.

Example 8

(41) Preparation of Cartridge, Hemolytic Agent, Nucleic Acid-Solubilizing Reagent A1, Washing Solution A and Recovering Solution A In the same manner as in Example 7, a cartridge, a hemolytic agent A, a nucleic acid-solubilizing reagent A1, a washing solution A and a recovering solution A were prepared.

(42) Preparation of DNase Reaction Solution

DNase reaction solution A1 was prepared according to the following formulation indicated below.

| (DNase reaction solution A1 = final concentration of magnesium 2 mmol/L) | |
|---|---|
| DNase I, AmpGrade (Invitrogen Corporation) 1 × DNase I reaction buffer | 20 U |
| Tris-HCl (pH 8.4) | 20 mmol/L |
| MgCl$_2$ | 2 mmol/L |
| KCl | 50 mmol/L |

(43) Preparation of Nucleic Acid Mixture Solution

Human whole blood, which was treated with EDTA-2Na as an anticoagulant, (the total number of leukocyte of 1×10$^7$, 2×10$^7$ and 3×10$^7$) was transferred to 50 mL-conical tube, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 2000×g for 2 minutes at 4° C., and then the supernatant solution was completely removed. After removing the supernatant solution, the hemolytic agent A in the amount of twice the amount of the original whole blood was added into the container. Light Vortex mixing was carried out for 5 seconds to suspend the cells, centrifuged at 2000×g for 2 minutes at 4° C., and then the supernatant solution was completely removed. To the leukocyte pellets obtained in the above, 520 μl of the nucleic acid-solubilizing reagent A1 was added, and leukocyte was dissolved by stirring using a Vortex mixer for 30 seconds. Here, 250 μl of 99.5 vol % or more superhigh-grade ethanol was added. That is, the concentration of ethanol became 32.5 vol %, and then the solution was stirred using a Vortex mixer for 30 seconds.

(44) Operation for Separating and Purifying RNA

The mixture solution of nucleic acid obtained from the above was injected into one opening of the cartridge for separation and purification of nucleic acid having the nucleic acid-adsorbing porous membrane prepared in (41) above, subsequently, a pressure difference-generating apparatus was connected to the one opening to make an inside of the cartridge for separation and purification of nucleic acid into a pressurized state. The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 of the washing solution A was injected into the one opening of the cartridge for separation and purification of nucleic acid, then a pressure difference-generating apparatus was connected to the one opening to make the inside of the cartridge for separation and purification of nucleic acid into a pressurized state. The injected washing solution was passed through the nucleic acid-adsorbing porous membrane and discharged from another opening. To the one opening, 40 μl of DNase solution A1 was injected, and the mixture was incubated for 15 minutes at room temperature. Thereafter, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state. The injected washing solution was passed through the nucleic acid-adsorbing porous membrane and discharged from another opening. The same operation was repeated twice. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state. The injected recovering solution was passed through the nucleic acid-adsorbing porous membrane, discharged from another opening, thereby the eluted solution was recovered. The time needed to operate separation and purification of RNA was less than 18 minutes, which includes DNase reaction time, per 1 sample in each number of white blood cells.

(45) Yield and Purity of Recovered Nucleic Acid

The yield and purity (260/280) of RNA recovered in Example 8 are presented in Table 8.

TABLE 8

| Number of white blood cells | Concentration of magnesium in DNase reaction solution [mmol/L] | Yield of RNA [μg] | 260/280 |
|---|---|---|---|
| $1 \times 10^7$ | 2 | 4.5 | 2.2 |
| $2 \times 10^7$ | 2 | 7.0 | 2.2 |
| $3 \times 10^7$ | 2 | 10.6 | 2.2 |

Therefore, DNA was completely removed by the DNase treatment, and it was possible to recover high purity RNA conveniently from leukocyte.

Example 9

(46) Preparation of Cartridge, Hemolytic Agent, Nucleic Acid-Solubilizing Reagent A1, Washing Solution A and Recovering Solution A In the same manner as in Example 7, a cartridge, a hemolytic agent A, a nucleic acid-solubilizing reagent A1, a washing solution A and a recovering solution A were prepared.

(47) Preparation of DNase Reaction Solution

DNase reaction solution A2 was prepared according to the following formulation indicated below.

| (DNase reaction solution A2 = final concentration of magnesium 102 mmol/L) | |
|---|---|
| DNase I, AmpGrade (Invitrogen Corporation) | 20 U |
| 1 × DNase I reaction buffer | |
| Tris-HCl (pH 8.4) | 20 mmol/L |
| $MgCl_2$ | 2 mmol/L |
| KCl | 50 mmol/L |
| 1 M $MgCl_2$ | 0.1 mmol/L |

(48) Preparation of Nucleic Acid Mixture Solution

Human whole blood, which was treated with EDTA-2Na as an anticoagulant, (the total number of leukocyte of $1 \times 10^7$, $2 \times 10^7$ and $3 \times 10^7$) was transferred to 50 mL-conical tube, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 2000×g for 2 minutes at 4° C., and then the supernatant solution was completely removed. After removing the supernatant solution, the hemolytic agent A in the amount of twice the amount of the original whole blood was added into the container. Light Vortex mixing was carried out for 5 seconds to suspend the cells, centrifuged at 2000×g for 2 minutes at 4° C., and then the supernatant solution was completely removed. To the leukocyte pellets obtained in the above, 520 μl of the nucleic acid-solubilizing reagent A1 was added, and leukocyte was dissolved by stirring using a Vortex mixer for 30 seconds. Here, 250 μl of 99.5 vol % or more superhigh-grade ethanol was added. That is, the concentration of ethanol became 32.5 vol %, and then the solution was stirred using a Vortex mixer for 30 seconds.

(49) Operation for Separating and Purifying RNA

The mixture solution of nucleic acid obtained from the above was injected into one opening of the cartridge for separation and purification of nucleic acid having the nucleic acid-adsorbing porous membrane prepared in (46) above, subsequently, a pressure difference-generating apparatus was connected to the one opening to make an inside of the cartridge for separation and purification of nucleic acid into a pressurized state. The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state. The injected washing solution was passed through the nucleic acid-adsorbing porous membrane and discharged from another opening. To the one opening, 40 μl of DNase solution A2 was injected, and the mixture was incubated for 15 minutes at room temperature. Thereafter, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state. The injected washing solution was passed through the nucleic acid-adsorbing porous membrane and discharged from another opening. The same operation was repeated twice. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state. The injected recovering solution was passed through the nucleic acid-adsorbing porous membrane, discharged from another opening, thereby the eluted solution was recovered. The time needed to operate separation and purification of RNA was less than 17 minutes, which includes DNase reaction time, per 1 sample in each number of white blood cells.

(50) Yield and Purity of Recovered Nucleic Acid

The yield and purity (260/280) of RNA recovered in Example 9 are presented in Table 9.

TABLE 9

| Number of white blood cells | Concentration of magnesium in DNase reaction solution [mmol/L] | Yield of RNA [μg] | 260/280 |
|---|---|---|---|
| $1 \times 10^7$ | 102 | 4.7 | 2.2 |
| $2 \times 10^7$ | 102 | 9.0 | 2.2 |
| $3 \times 10^7$ | 102 | 11.4 | 2.1 |

Therefore, DNA was completely removed by the DNase treatment, and it was possible to recover high purity RNA conveniently from leukocyte.

Example 10

(51) Preparation of Cartridge, Hemolytic Agent, Nucleic Acid-Solubilizing Reagent A1, Washing Solution A and Recovering Solution A In the same manner as in Example 7, a cartridge, a hemolytic agent A, a nucleic acid-solubilizing reagent A1, a washing solution A and a recovering solution A were prepared.

(52) Preparation of DNase Reaction Solution

DNase reaction solution A3 was prepared according to the following formulation indicated below.

| (DNase reaction solution A3 = final concentration of magnesium 102 mmol/L) | |
|---|---|
| DNase I, AmpGrade (Invitrogen Corporation) | 20 U |
| 1 × DNase I reaction buffer | |
| Tris-HCl (pH 8.4) | 20 mmol/L |
| $MgCl_2$ | 2 mmol/L |
| KCl | 50 mmol/L |
| 1 M $MgSO_4$ | 0.1 mmol/L |

(53) Preparation of Nucleic Acid Mixture Solution

Human whole blood, which was treated with EDTA-2Na as an anticoagulant, (the total number of leukocyte of $2 \times 10^7$ and $3 \times 10^7$) was transferred to 50 mL-conical tube, and the hemolytic agent A in the amount of 5 times the amount of each whole blood was added respectively thereto and incubated on ice for 15 minutes. During the incubation, Vortex mixing was carried out twice. The blood suspension becoming transparent was confirmed, centrifuged at 2000×g for 2 minutes at 4° C., and then the supernatant solution was completely removed. After removing the supernatant solution, the hemolytic agent A in the amount of twice the amount of the original whole blood was added into the container. Light Vortex mixing was carried out for 5 seconds to suspend the cells, centrifuged at 2000×g for 2 minutes at 4° C., and then the supernatant solution was completely removed. To the leukocyte pellets obtained in the above, 520 μl of the nucleic acid-solubilizing reagent A1 was added, and leukocyte was dissolved by stirring using a Vortex mixer for 30 seconds. Here, 250 μl of 99.5 vol % or more superhigh-grade ethanol was added. That is, the concentration of ethanol became 32.5 vol %, and then the solution was stirred using a Vortex mixer for 30 seconds.

(54) Operation for Separating and Purifying RNA

The mixture solution of nucleic acid obtained from the above was injected into one opening of the cartridge for separation and purification of nucleic acid having the nucleic acid-adsorbing porous membrane prepared in (34) and (35) above, subsequently, a pressure difference-generating apparatus was connected to the one opening to make an inside of the cartridge for separation and purification of nucleic acid into a pressurized state. The injected sample solution containing nucleic acid was contacted with the nucleic acid-adsorbing porous membrane by passing the injected sample solution containing nucleic acid through the nucleic acid-adsorbing porous membrane and discharged from another opening of the cartridge for separation and purification of nucleic acid. Subsequently, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state. The injected washing solution was passed through the nucleic acid-adsorbing porous membrane and discharged from another opening. To the one opening, 40 μl of DNase solution A3 was injected, and the mixture was incubated for 15 minutes at room temperature. Thereafter, 750 μl of the washing solution A was injected into the one opening of the cartridge for separation and purification of nucleic acid, then a pressure difference-generating apparatus was connected to the one opening to make the inside of the cartridge for separation and purification of nucleic acid into a pressurized state. The injected washing solution was passed through the nucleic acid-adsorbing porous membrane and discharged from another opening. The same operation was repeated twice. Next, 50 μl of the recovering solution A was injected into the one opening of the cartridge for separation and purification of nucleic acid, and a pressure difference-generating apparatus was connected to the one opening of the cartridge for separation and purification of nucleic acid to make the inside of the cartridge for separation and purification of nucleic acid into a pressurized state. The injected recovering solution was passed through the nucleic acid-adsorbing porous membrane, discharged from another opening, thereby the eluted solution was recovered. The time needed to operate separation and purification of RNA was less than 18 minutes, which includes DNase reaction time, per 1 sample in each number of white blood cells.

(55) Yield and Purity of Recovered Nucleic Acid

The yield and purity (260/280) of RNA recovered in Example 10 are presented in Table 10.

TABLE 10

| Number of white blood cells | Concentration of magnesium in DNase reaction solution [mmol/L] | Yield of RNA [μg] | 260/280 |
|---|---|---|---|
| $2 \times 10^7$ | 102 | 8.4 | 2.1 |
| $3 \times 10^7$ | 102 | 13.3 | 2.2 |

Therefore, DNA was completely removed by the DNase treatment, and it was possible to recover high purity RNA conveniently from leukocyte.

INDUSTRIAL APPLICABILITY

According to the present invention, RNA can be obtained with high efficiency and high purity, for example, as an aqueous RNA solution by separating a leukocyte from blood.

Further, RNA can be separated and purified from the test sample according to the method for separating and purifying RNA of the invention with excellent separating capability, convenience, rapidness and automation capability.

The entire disclosure of each and every foreign patent application from which the benefit of foreign priority has been claimed in the present application is incorporated herein by reference, as if fully set forth.

The invention claimed is:

1. A method for separating and purifying RNA comprising:
   (1) passing a sample solution containing a nucleic acid through a nucleic acid-adsorbing porous membrane to adsorb the nucleic acid to the porous membrane;
   (2) passing a washing solution through the nucleic acid-adsorbing porous membrane to wash the porous membrane while adsorbing the nucleic acid; and
   (3) passing a recovering solution through the nucleic acid-adsorbing porous membrane to desorb the nucleic acid from the porous membrane,
   wherein the nucleic acid adsorbing porous membrane is a porous membrane capable of adsorbing a nucleic acid by interaction involving substantially no ionic bond, and
   wherein the sample solution containing the nucleic acid is obtained by a process for preparing a sample solution, the process comprising:
   (I) injecting a test sample containing: at least one of blood and leukocyte; and an anticoagulant to a container;
   (II) adding a hemolytic agent to the container and after adding the hemolytic agent, carrying out a centrifugation to obtain a leukocyte pellet;
   (III) adding a nucleic acid-solubilizing reagent to the leukocyte pellet to obtain a mixture solution; and
   (IV) adding a water-soluble organic solvent to the mixture solution to obtain the sample solution containing the nucleic acid.

2. The method for separating and purifying RNA according to claim 1,
   wherein the hemolytic agent comprises at least one selected from ammonium chloride, sodium chloride, ammonium oxalate and saponin.

3. The method for separating and purifying RNA according to claim 1,
   wherein after adding the hemolytic agent in the step (II), an incubation is carried out at 0 to 35° C.

4. The method for separating and purifying RNA according to claim 1,
   wherein the nucleic acid-solubilizing reagent comprises at least one selected from a chaotropic salt, a nucleic acid stabilizing agent, a surfactant, a buffering agent and a defoaming agent.

5. The method for separating and purifying RNA according to claim 4,
   wherein the chaotropic salt is a guanidinium salt.

6. The method for separating and purifying RNA according to claim 4,
   wherein the nucleic acid stabilizing agent is a reducing agent.

7. The method for separating and purifying RNA according to claim 4,
   wherein the surfactant includes a nonionic surfactant.

8. The method for separating and purifying RNA according to claim 1,
   wherein at least one of the sample solution containing the nucleic acid, the washing solution and the recovering solution is passed through the nucleic acid-adsorbing porous membrane under a pressurizing condition.

* * * * *